US012220284B2

(12) United States Patent
Heacock

(10) Patent No.: US 12,220,284 B2
(45) Date of Patent: Feb. 11, 2025

(54) COLOR SENSOR WITH GAS GENERATING LAYER

(71) Applicant: THERMOGRAPHIC MEASUREMENTS LIMITED, Connah's Quay (GB)

(72) Inventor: Gregory Heacock, Maple Valley, WA (US)

(73) Assignee: THERMOGRAPHIC MEASUREMENTS LIMITED (GB)

(*) Notice: Subject to any disclaimer, the term of this patent is extended or adjusted under 35 U.S.C. 154(b) by 0 days.

(21) Appl. No.: 15/295,431

(22) Filed: Oct. 17, 2016

(65) Prior Publication Data
US 2018/0104017 A1 Apr. 19, 2018

(51) Int. Cl.
A61B 90/00 (2016.01)
G01N 21/78 (2006.01)
G01N 21/80 (2006.01)
G01N 31/22 (2006.01)

(52) U.S. Cl.
CPC ........... A61B 90/08 (2016.02); G01N 21/783 (2013.01); G01N 21/80 (2013.01); G01N 31/223 (2013.01); G01N 31/229 (2013.01); A61B 2090/081 (2016.02); G01N 31/221 (2013.01); G01N 31/225 (2013.01)

(58) Field of Classification Search
CPC .. A61B 90/08; A61B 2090/081; G01N 21/80; G01N 21/783; G01N 31/229; G01N 31/223; G01N 31/221; G01N 31/225
See application file for complete search history.

(56) References Cited

U.S. PATENT DOCUMENTS

| 3,018,611 A | 1/1962 | Biritz |
| 2,768,976 A | 10/1973 | Hu |
| 3,768,976 A | 10/1973 | Hu |
| 3,899,295 A | 8/1975 | Halperin |
| 3,939,968 A | 2/1976 | Ryder |

(Continued)

FOREIGN PATENT DOCUMENTS

| CN | 101479584 | 7/2009 |
| CN | 101501468 | 8/2009 |

(Continued)

OTHER PUBLICATIONS

Michael Freemantle, Intelligence Ink Detects Oxygen, Chemical Gas Sensing, Aug. 2, 2004, p. 11, vol. 82, No. 31, Chemical & Engineering News USA (2 pages).

(Continued)

Primary Examiner — Lore R Jarrett
(74) Attorney, Agent, or Firm — Jackson Walker LLP

(57) ABSTRACT

According to embodiments of the present application, a color change sensor comprises a color change indicator and a substrate comprising a gas disposed on the color change indicator. The sensor may further comprise an interface layer that assists in containing the gas within the substrate. The sensor may be used with limited use, restricted use, or disposable apparatuses. The user may actuate the sensor by disrupting or removing the gas-containing substrate and/or the interface layer. Methods of making and using the color change sensor and related apparatuses are also disclosed.

18 Claims, 25 Drawing Sheets
(14 of 25 Drawing Sheet(s) Filed in Color)

(56) References Cited

U.S. PATENT DOCUMENTS

| | | | |
|---|---|---|---|
| 4,003,709 A | 1/1977 | Eaton | |
| 4,098,577 A | 7/1978 | Halpem | |
| 4,135,792 A | 1/1979 | Deeg et al. | |
| 4,526,752 A | 7/1985 | Perlman et al. | |
| 4,692,309 A | 9/1987 | Pannwitz | |
| 4,728,499 A | 3/1988 | Fehder | |
| 5,159,360 A | 10/1992 | Stoy et al. | |
| 5,375,592 A * | 12/1994 | Kirk | A61M 16/0488 116/206 |
| 5,518,927 A | 5/1996 | Malchesky et al. | |
| 5,549,924 A * | 8/1996 | Shlenker | A61F 6/04 427/407.1 |
| 5,623,323 A | 4/1997 | Johnson et al. | |
| 5,706,073 A | 1/1998 | Volk | |
| 5,942,438 A | 8/1999 | Antonoplos et al. | |
| 6,060,210 A | 5/2000 | Eda et al. | |
| 6,114,509 A | 9/2000 | Olsen et al. | |
| 6,132,086 A | 10/2000 | Henwood | |
| 6,218,189 B1 | 4/2001 | Antonoplos et al. | |
| 6,254,969 B1 | 7/2001 | Eberle | |
| 6,270,724 B1 | 8/2001 | Woodaman | |
| 6,518,231 B2 | 2/2003 | Appel et al. | |
| 6,634,747 B1 | 10/2003 | Atkins et al. | |
| 6,634,753 B1 | 10/2003 | Rozenman | |
| 6,710,221 B1 | 3/2004 | Pierce et al. | |
| 6,790,411 B1 | 9/2004 | Forest et al. | |
| 6,851,808 B2 | 2/2005 | Heacock | |
| 7,219,799 B2 | 5/2007 | Bonnette et al. | |
| 7,244,252 B2 | 7/2007 | Berndt | |
| 7,785,299 B2 | 8/2010 | Crawford et al. | |
| 8,137,303 B2 | 3/2012 | Crawford et al. | |
| 8,163,237 B2 | 4/2012 | Crawford et al. | |
| 8,257,663 B2 | 9/2012 | Crawford et al. | |
| 8,338,131 B2 | 12/2012 | Callen et al. | |
| 8,388,131 B2 | 3/2013 | Heacock et al. | |
| 8,663,998 B2 | 3/2014 | Heacock | |
| 9,013,102 B1 * | 4/2015 | Wedding | H01J 11/18 250/374 |
| 9,746,421 B2 | 8/2017 | Heacock | |
| 2002/0022008 A1 | 2/2002 | Forest et al. | |
| 2002/0023642 A1 | 2/2002 | Holmsten et al. | |
| 2002/0137123 A1 | 9/2002 | Hui | |
| 2003/0199095 A1 | 10/2003 | Yuyama et al. | |
| 2004/0115319 A1 | 6/2004 | Morris | |
| 2004/0180391 A1 | 9/2004 | Gratzl et al. | |
| 2004/0265440 A1 | 12/2004 | Morris et al. | |
| 2005/0041200 A1 | 2/2005 | Rich | |
| 2005/0125924 A1 | 6/2005 | Benjamin et al. | |
| 2005/0164898 A1 | 7/2005 | Kalsuri et al. | |
| 2006/0046301 A1 | 3/2006 | Happe | |
| 2006/0054525 A1 | 3/2006 | Dean et al. | |
| 2006/0054526 A1 | 3/2006 | Dean | |
| 2006/0069305 A1 | 3/2006 | Couvillon, Jr. et al. | |
| 2006/0110835 A1 | 5/2006 | Gohil | |
| 2006/0166177 A1 * | 7/2006 | Hageman | G09B 23/24 434/276 |
| 2006/0181676 A1 | 8/2006 | Tucker et al. | |
| 2006/0236913 A1 | 10/2006 | Willis | |
| 2007/0017042 A1 | 1/2007 | Cincotta et al. | |
| 2007/0140911 A1 | 6/2007 | Carney et al. | |
| 2008/0004389 A1 * | 1/2008 | Rho | C08L 83/04 524/430 |
| 2008/0081020 A1 | 4/2008 | Huang | |
| 2008/0129960 A1 | 6/2008 | Heacock et al. | |
| 2009/0011044 A1 * | 1/2009 | Gutman | A23L 3/34 424/613 |
| 2009/0266289 A1 | 10/2009 | Greene | |
| 2009/0301382 A1 | 12/2009 | Patel | |
| 2009/0303440 A1 | 12/2009 | Heacock et al. | |
| 2010/0112680 A1 | 5/2010 | Brockwell et al. | |
| 2011/0130727 A1 | 6/2011 | Crawford et al. | |
| 2011/0130728 A1 | 6/2011 | McKinnon et al. | |
| 2011/0259086 A1 | 10/2011 | Harris et al. | |
| 2012/0135527 A1 * | 5/2012 | Bangera | G08B 21/245 436/3 |
| 2012/0276647 A1 | 11/2012 | Mills | |
| 2013/0130399 A1 | 5/2013 | Mills et al. | |
| 2013/0150785 A1 | 6/2013 | Heacock | |
| 2013/0269592 A1 | 10/2013 | Heacock et al. | |
| 2013/0293353 A1 | 11/2013 | McPherson | |
| 2014/0296402 A1 | 10/2014 | Jung et al. | |
| 2014/0326134 A1 * | 11/2014 | Frankel | B01D 53/0407 95/25 |
| 2015/0087076 A1 | 3/2015 | Heacock | |
| 2015/0225304 A1 | 8/2015 | Donze et al. | |
| 2015/0253252 A1 * | 9/2015 | Smyth | G01N 31/225 422/429 |
| 2015/0346513 A1 | 12/2015 | Heacock | |
| 2016/0011157 A1 | 1/2016 | Smyth et al. | |
| 2016/0327491 A1 | 11/2016 | Wood | |

FOREIGN PATENT DOCUMENTS

| | | |
|---|---|---|
| CN | 105954280 A | 9/2016 |
| EP | 0231499 | 8/1987 |
| EP | 2021755 | 5/2007 |
| JP | 2002309191 A | 10/2002 |
| WO | 02099416 A1 | 12/2002 |
| WO | 2004077035 A1 | 9/2004 |
| WO | 2006058228 A1 | 6/2006 |
| WO | 2007018301 | 2/2007 |
| WO | 2007134066 A2 | 11/2007 |
| WO | 2008095960 A1 | 8/2008 |
| WO | 2008067143 A3 | 10/2008 |
| WO | 2013085655 A1 | 6/2013 |
| WO | 2015048138 | 4/2015 |

OTHER PUBLICATIONS

Swann et al., "Designing Out Curative Syringe Reuse: Maximising Global Acceptance and Impact by Design," Internet Citation, http://eprints.hud.ac.uk/11783/ [dated Sep. 18, 2013] abstract.

The Guardian, Architecture and Design Blog with Oliver Wainwright, "How colour-changing technology could revolutionise the medical industry," Internet Citation, http://www.theguardian.cco/artanddesign/architectarc-design-blog/2013/Aug. 28/colour-changing-syringe-medical-design [dated Sep. 18, 2013].

Extended European Search Report, Application No. 17196898.5 dated Jul. 27, 2018.

Partial Search Report, Application No. 17196898.5 dated Apr. 12, 2018.

European Patent Office Communication Pursuant to Art. 94(3) EPC dated Dec. 16, 2021, 9 pages.

* cited by examiner

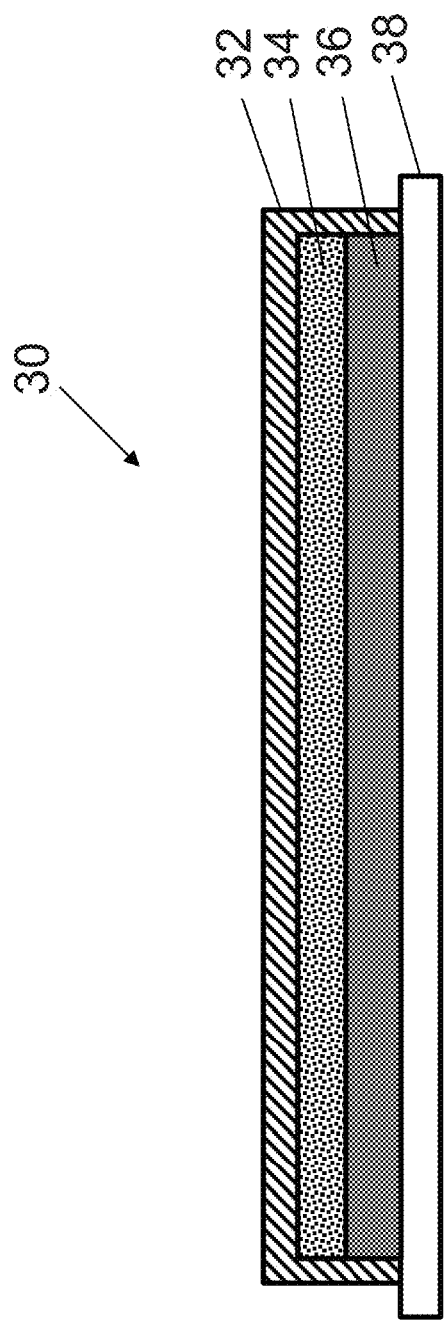

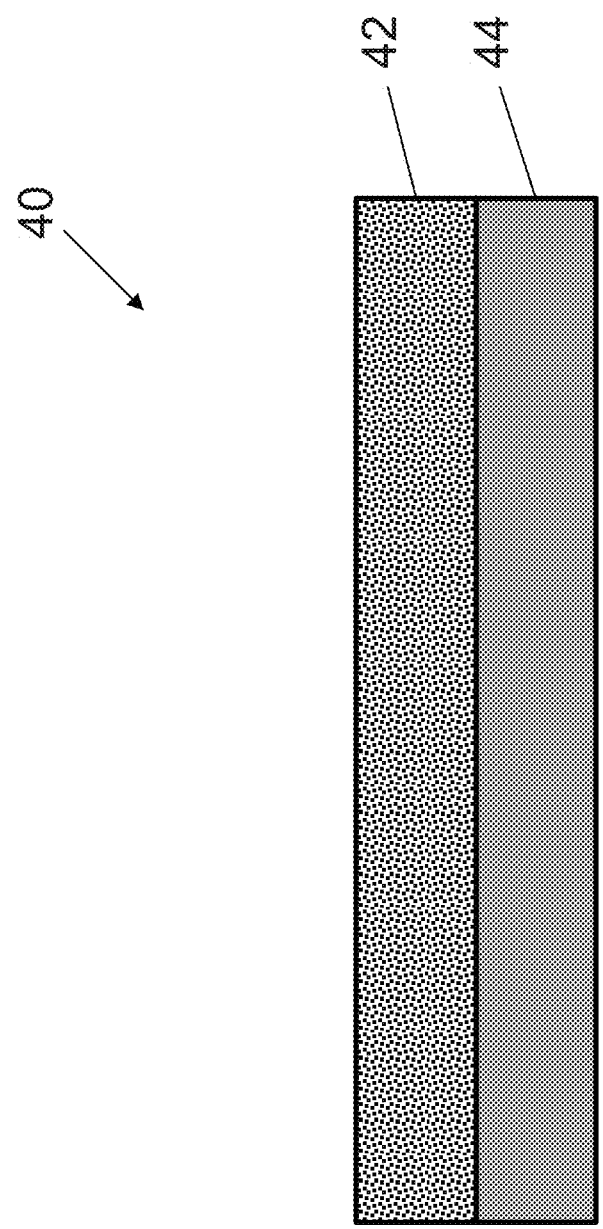

COLOR SENSOR WITH GAS GENERATING LAYER

CROSS-REFERENCE TO RELATED APPLICATIONS

[Not Applicable]

FEDERALLY SPONSORED RESEARCH OR DEVELOPMENT

[Not Applicable]

BACKGROUND OF THE APPLICATION

Many products currently marketed and sold to consumers are designed for limited use. These products are usually associated with a single event, a restricted time period or restricted access. There are many reasons for the need of single use or limited use products.

There are numerous examples of single use products in the medical field. One example is a disposable syringe. Instrument contamination and cross infection between patients is an ever present concern if the syringe is inadvertently reused. It is a particular concern in some countries where repeated use of instruments is known to transmit serious diseases such as HIV and hepatitis. Medical and ophthalmic devices that must be sterilized such as scalpels or tonometers (e.g., for the measurement of a patient's intraocular pressure) and body piercing and tattooing instruments used on multiple clients also give cause for concern. Needles used in acupuncture offer another example. Decontamination procedures or employment of single-use devices are methods used to control cross infection, but they rely on personnel awareness, willingness to follow protocol, monitoring and documentation.

The limited use type of product is usually associated with goods that should be used for a restricted time period. One example is products that have a shelf life after which they should not be used because of a risk of infection or a decrease in effectiveness are cosmetic products, personal hygiene products such as electric toothbrush heads, and home diagnostic kits such as pregnancy tests and ovulation prediction tests. For example, it has been found that cosmetic applicators can harbor bacteria that can infect the eye and should be disposed of prior to their expiration to prevent eye infections.

Many products currently marketed and sold to consumers are supplied prepackaged where the packaging is intended to preserve the freshness of the product such as food or beverages or in the case of medication, the potency of the content within the packaging. These products are usually associated with a single event, i.e., the contents remain fresh or potent until the packaging is opened by the consumer; however, the freshness or quality of the contents may decrease over time.

An example of the importance of preservation of a packaged product is a cold tablet or a food item. Medicinal potency or food spoilage and the expense related to these issues are important to both consumers and manufacturers. Pharmaceuticals, food stuff, and similar items are commonly packaged in sealed plastic containers.

Gas permeation through the plastic material of the container (e.g., oxygen) negatively affects the freshness or quality of the contents of many packaged products. In the case of pharmaceuticals, oxygen absorption and subsequent reaction, decreases potency. In the case of food products, oxygen absorption into the packaged food promotes the growth of many food spoilage microbes which can cause a loss of product quality, including freshness and safeness to eat.

Moreover, products may have different intended uses and may have different times after which the product should no longer be used based on the intended use. For example, a single medical device could have many different uses. Depending on the use, the medical device should be changed after a different period of time. For example, a catheter could be used in one way where it should be changed after 72 hours but when used another way would not need to be changed until 96 or 168 hours. Medications could also have a different shelf life based on different uses. For example, maximum potency might be required for a certain use while a decline in potency would be acceptable for an alternate use. Foods could similarly have a different shelf life based on their intended use. The same food product might be deemed acceptable for consumption by a pet longer than it would be deemed acceptable for consumption by a human.

Various color change indicators and related apparatuses, as well as disposable, limited, and restricted use apparatuses, have been described in applications and patents co-owned by applicant. These color change indicators may be used to assess the condition of a disposable, limited use, or restricted use apparatus.

For example, U.S. Pat. Nos. 8,388,131 and 9,134,285 and U.S. patent application Ser. No. 14/292,246, and their related cases, which are incorporated herein in its entirety by reference, describe color change indicators that may be used to indicate the condition of particular products. U.S. Pat. No. 8,388,131, and its related cases presented, for example, a disposable limited or restricted use apparatus that includes a color changeable portion wherein the time that the color change occurs is controlled so that it coincides to the approximate time of the end of one use of a single use apparatus or to the approximate expiration time for extended but limited or restricted use apparatus. U.S. patent application Ser. No. 14/292,246, for example, describes carbon dioxide sensing color change indicators for use with disposable, limited use, or restricted use apparatuses.

U.S. Pat. No. 8,663,998, and its related case, which are incorporated herein in its entirety by reference, also describe color change indicators. U.S. Pat. No. 8,663,998 presented, for example, a color changeable dye that can include a redox indicator, a reduction reaction initiator, an electron donor, an oxygen scavenger, an indicator barrier agent, a thickening agent and an agent to facilitate mixing. The color changeable dye may be, for example, a first color in the presence of oxygen, capable of changing to a second color upon reduction in a substantially oxygen free environment, and capable of changing back to the first color after exposure to oxygen for a period of time corresponding to the intended use time of a disposable or limited use product.

U.S. patent application Ser. No. 14/038,586, which is co-owned by applicant and incorporated herein in its entirety, presented, for example, use protocol indicators having a color changeable dye that changes color after exposure to a particular environment for a defined time. U.S. patent application Ser. No. 14/038,586 is also directed to, for example, an exposure time indicator that uses a color changeable dye or multiple color changeable dyes that change color after exposure to an environment in a sequential manner.

In some cases, a color change indicator may be disposed on a disposable, restricted, or limited use product and be directly exposed to the atmosphere. This exposure affects activation of the color change indicator and the indicator changes color after exposure to the environment. In other cases, a color change indicator may be disposed on a product, which itself is inside separate packaging, e.g., plastic packaging such as a Tyvek pouch. The separate packaging may be filled with a gas, such as carbon dioxide, to protect the product from microbial growth (carbon dioxide is an active packaging gas for reducing microbial growth), and also prevent the color indicator from activation. However, because the separate packaging is often permeable to some degree, atmospheric gases such as oxygen and carbon dioxide permeate through the packaging, thus, eventually allowing the indicator to become exposed to the atmosphere. For example, a Tyvek pouch may be flood-filled with carbon dioxide to protect an apparatus within the pouch and a color change indicator thereon; however, the Tyvek pouch is permeable to carbon dioxide. This permeation affects the activation of the color change indicator. In other words, the color change indicator is activated as soon as the indicator becomes exposed to the atmosphere, whether directly or indirectly.

In many cases, it is desirable to have the color change indicator reflect that the product has been exposed to the atmosphere or a particular environment for a particular period or time or at a particular level. However, in some cases, there is a need to delay the color change or further prevent activation of the color change indicator.

Barriers such as those described in U.S. patent application Ser. Nos. 14/038,586 and 14/292,246, which are hereby incorporated by reference, that are placed on the color changeable dye assist in slowing or delaying color change and may also be used to achieve color change at different times. However, these barriers are permeable and, while their use delays color change, there is a need for additional solutions which further extend the life of the indicator and allow for user flexibility in activation or initiation of the color change, allow the user to control activation of the indicator, or allow the user to determine when he or she wants to trigger the start of the color change process.

The present application generally speaking describes a color changing sensor that delays color change via a self-contained gas layer or gas-containing substrate that interferes with the exposure of the color change indicator to atmospheric conditions and/or allows for activation of the color change sensor by the user. The gas layer or gas-containing substrate further enhances the life of the indicator while allowing for greater flexibility in user control and product packaging allowing the apparatus to be used with both permeable and non-permeable product packaging and even no product packaging.

SUMMARY OF THE INVENTION

The present application relates to a color changing sensor that comprises a substrate comprising a gas disposed on a color change indicator. Generally speaking, the present application relates to a sensor comprising a substrate comprising non-atmospheric levels of a gas disposed (directly or indirectly) on a color change indicator. This gas-containing substrate or gas layer is disposed such that it limits or inhibits exposure of the color change indicator to atmospheric conditions. The substrate may comprise any appropriate gas including carbon dioxide, oxygen, argon, nitrogen, or ammonia that will assist in inhibiting permeation of atmosphere. For example, the substrate may contain higher than atmospheric levels of carbon dioxide, nitrogen, argon, or ammonia. As another example, the substrate may contain higher or lower than atmospheric levels of oxygen. In one embodiment, the gas in the gas layer may be dispersed in a substrate such as a gas containing-matrix. In one embodiment, the gas-containing matrix comprises polymethylmethacrylate, silicone, or urethane. In another embodiment, the substrate comprises a gas-generating component. The gas-generating component may be combined with another gas-generating component and provides or generates gas for the gas-containing substrate or gas-layer.

The color change indicator may be any appropriate color change indicator including those susceptible to change based on atmospheric conditions including carbon dioxide-based indicators, oxygen-based indicators, or ammonia-based indicators. Examples of color change indicators have been described in prior patents and patent applications, for example, as discussed above and herein.

In one embodiment of the present application, the color change indicator is a carbon dioxide-based indicator and the gas layer or gas-containing substrate comprises greater than atmospheric levels of carbon dioxide. In another embodiment, the color change indicator is an oxygen-based indicator and the gas layer or gas-containing substrate comprises greater than atmospheric levels of carbon dioxide, argon, or nitrogen. In one embodiment, the color change indicator is disposed on a substrate.

In one embodiment, the sensor further includes an interface layer. The interface layer may be directly or indirectly disposed on the gas layer or gas-containing substrate. The interface layer assists in containing the gas in the gas layer or gas-containing substrate. In other embodiments, the gas layer or gas-containing substrate is made from a material that itself contains the gas. In one embodiment, the sensor is activated by removing or disrupting at least a portion of the interface layer. In another embodiment, the sensor is activated by removing or disrupting at least a portion of the substrate.

In another embodiment, an adhesive or other separation layer may be disposed between the interface layer and the gas layer and/or between the gas layer and the color change indicator. In some embodiments, an adhesive is disposed between the substrate or gas layer and the color change indicator. In some embodiments, an adhesive may also be disposed between the interface layer and the substrate or between the substrate and the color change indicator. In other embodiments, the interface layer is disposed directly on the gas layer or substrate and/or the gas layer or substrate is disposed directly on the color change indicator.

In one aspect, the present application relates to an apparatus comprising a disposable, restricted or limited use apparatus and a sensor comprising an interface layer, a gas layer or substrate comprising a gas, and a color change indicator wherein the interface layer is disposed on the gas layer or substrate and the gas layer or substrate is disposed on the color change indicator. In another embodiment, the apparatus further includes a second color change indicator such as an indicator that allows the user to determine how long the disposable, limited use, or restricted use product has been exposed to atmospheric conditions or another environment. The second color change indicator may be disposed on the sensor.

In another aspect, the present application relates to a color change sensor comprising a first gas-generating component and a substrate comprising a second gas-generating component wherein the substrate is disposed on a color change indicator. In one embodiment, the substrate includes the first gas-generating component. The first and second gas-generating components may be two components that, when reacted, generate a gas such as carbon dioxide including, for example, sodium bicarbonate and acetic acid.

In another aspect, the present application relates to a kit comprising at least one substrate comprising non-atmospheric levels of a gas and at least one color change indicator and preferably more color change indicators. In this embodiment, the user can assemble a sensor and select a preferred indicator for a particular application. Alternatively, or in addition, the kit may comprise at least two sensors for selection by the user.

In one embodiment, once activated, the sensor changes color after being exposed to a particular environment for a predetermined period of time.

In another embodiment, the sensor is intended for use with disposable, limited or restricted use products including products that can transmit contaminants or disease to a person, cause infection, or decline in quality or potency if reused or used beyond a recommended period of time or packaging for a product for human consumption wherein the product for human consumption can decline in freshness, quality of taste, and/or potency and/or can cause disease if consumed beyond a recommended period of time. The sensor acts to indicate that a product should no longer be used or consumed.

The disposable, limited or restricted use product may have multiple uses that affect the lifespan of the product. The sensor may have a color changeable dye that changes color after exposure to a particular environment for a defined time. The defined time corresponds to, for example, the expiration time for a disposable, limited or restricted use product for a particular use or protocol(s) or the time after which a product should no longer be used or consumed.

In another embodiment, the sensor may include an exposure time indicator that uses a color changeable dye or multiple color changeable dyes that change color after exposure to an environment in a sequential manner. The exposure time indicator creates a spectrum that allows the user to see how much of the product's useful life has been used and how much remains.

One benefit of the invention is that, in some embodiments, it allows for a self-contained color change sensor that is protected from premature actuation and that can be used with a variety of disposable, limited use, or restricted use apparatuses. Another advantage is that, because the present invention allows for a self-contained sensor, it can be used independent of the packaging of the apparatuses with which it is used. In some embodiments, the sensor is disposed on a disposable, limited, or restricted use apparatus such as a medical device or is disposed on product packaging.

Another benefit of the invention is that, in some embodiments, the user may control activation of the color change sensor. In one embodiment, the user may activate the sensor by destroying or removing at least a portion of an interface layer which is disposed on the gas layer allowing gas from the gas layer to escape, exposing the color change indicator to the atmosphere. In another embodiment, the user may activate the sensor by destroying or removing the gas layer or both the interface layer and the gas layer, directly exposing the color change indicator to the atmosphere.

Another benefit of the invention is that, in one embodiment, flexibility is increased as it allows for later activation of the gas layer through the use of gas-generating components.

Another benefit of the invention is that, in some embodiments, an apparatus may comprise both the sensor of the present invention as well as a second color change indicator. This dual indicator embodiment allows a user, for example, to ascertain both the current status of the limited use, disposable, or restricted use apparatus using the color change indicator as well to separately deploy the product for a specific use by activating the sensor. In one embodiment, the second color change indicator is disposed on the sensor. For example, a color change indicator could be disposed on a sterile packaged catheter indicating the shelf life of the catheter and a sensor of the present invention could be disposed on the catheter, which may be actuated by the physician or nurse using the catheter, alerting the physician or nurse as to how long the catheter has been deployed in the patient. In one embodiment, the sensor is an exposure time indicator and the second color change indicator is a carbon dioxide based indicator.

These and other advantages and novel features of the present invention, as well as details of illustrated embodiments thereof will be more fully understood from the following description and from the figures.

BRIEF DESCRIPTION OF SEVERAL VIEWS OF THE DRAWINGS

The patent or application file contains at least one drawing executed in color. It is understood that copies of this patent or patent application publication with color drawing(s) will be provided by the Office upon request and payment of the necessary fee.

FIG. 3B is another illustration of another embodiment of a color change sensor comprising an interface layer, a gas layer or gas-containing substrate, a color change indicator, and a second substrate.

FIG. 4 is an illustration of another embodiment of the present invention showing a color change sensor comprising a gas layer or gas-containing substrate and a color change indicator.

Figure 1A:
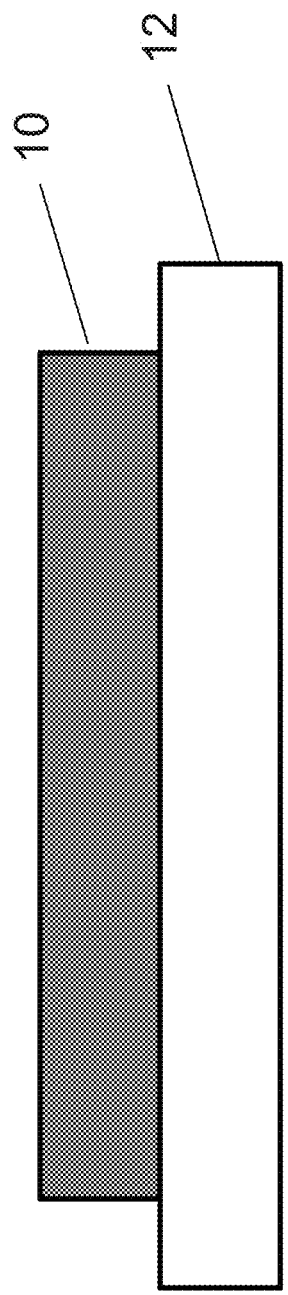
FIG. 1A is an illustration of a color change indicator disposed on a substrate.

The foregoing summary, as well as the following detailed description of certain embodiments of the present application, will be better understood when read in conjunction with the appended drawings. For the purposes of illustration, certain embodiments are shown in the drawings and described herein. It should be understood, however, that the claims are not limited to the arrangements and instrumentality shown in the attached drawings or the detailed description. Furthermore, the appearance shown in the drawings is one of many ornamental appearances that can be employed to achieve the stated functions of the system.

DETAILED DESCRIPTION

A color change indication on a product provides accurate information or a warning to a user of, e.g., prior use of a single use product or instrument; a reminder that a limited use product has neared or reached its expiration time; that a product that is restricted for use has been tampered with; or that a limited use product has been used for a particular period of time. The warning indication is provided by a color change indicator that changes color in a time controlled manner.

Figure 1B:
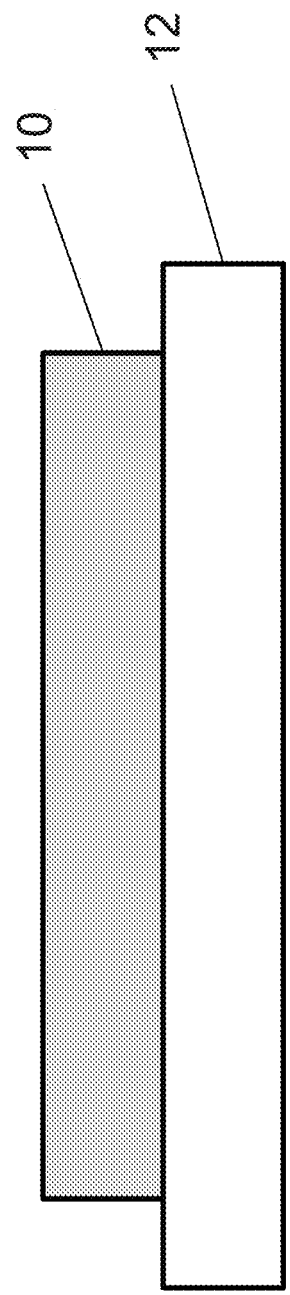
FIG. 1B is an illustration of the color change indicator of FIG. 1A after exposure to atmospheric conditions.

FIG. 1A depicts a color change indicator 10 having a first color and disposed on a substrate 12. A color change indicator such as that shown in FIG. 1A is directly exposed to the atmosphere and will thus begin to change color after conditions triggering the color change have been satisfied, e.g., after the indicator has been exposed to a particular environment for a certain amount of time. For example, if the indicator is an oxygen-based indicator, it may begin to change color as soon as it is exposed to the atmosphere. FIG. 1B depicts the color change indicator of FIG. 1A after the color change indicator 10 has changed to a second color after exposure to atmospheric conditions.

Figure 2:
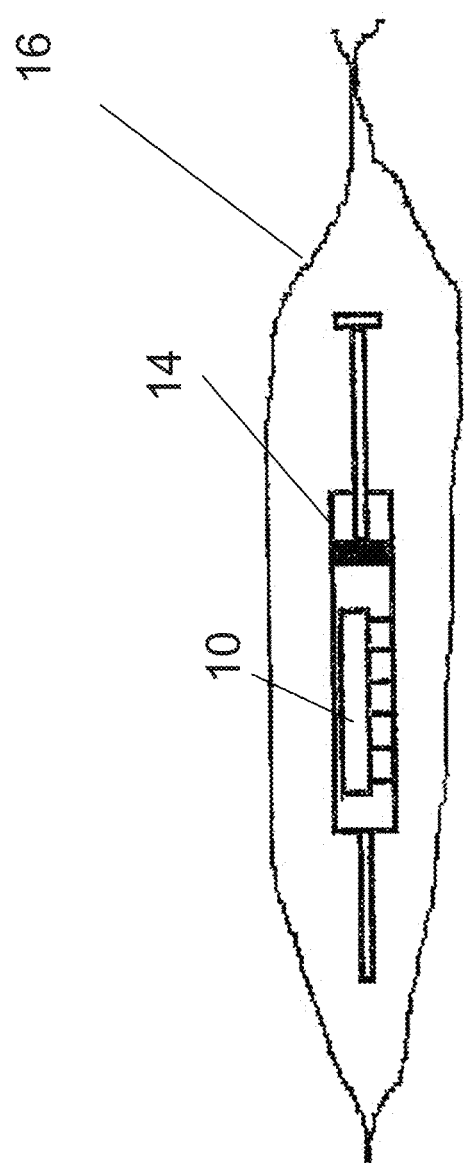
FIG. 2 is a perspective view of a syringe contained in a package to prevent premature actuation of the color changeable color change indicator.

The color change indicator can be disposed on the product itself by being either printed on the product or incorporated into the product or within the material forming a portion of the product. The color change indicator can also be disposed on or incorporated into a packaging or other article that accompanies the product. The product can then be subsequently packaged to provide a sterile environment for the product or limited access thereto. The internal atmosphere of the package is an inert gas, carbon dioxide, or a vacuum such that the package provides a sealed environment free of substances that trigger the color change of the dye, such as oxygen, carbon dioxide, nitrogen, water, etc. When the package is subsequently opened and the product is exposed to a trigger substance, such as atmospheric oxygen, the dye disposed on the product will change from a first color (often translucent or somewhat translucent, i.e. a milky white or "water white") to a second color (often a blue or red color) after a period of time that is controlled by the composition of the dye and other factors, and that is selected to correspond to the typical time for a single use of a product in the case of single use products or that corresponds to the expiration time of the product. For example, FIG. 2 depicts a disposable syringe 14 with a color change indicator 10 disposed thereon. The syringe 14 is sealed within package 16, which delays activation of the color change indicator. The time at which the dye changes color can also be selected so as to indicate that the product may have been tampered with. Moreover, the timing of the color change can be further delayed by incorporating features described herein including, for example, barriers or barrier agents that inhibit the chemistry that causes the color change.

However, as discussed above, while such features are able to delay color change, atmospheric gases may permeate through packaging triggering the color change indicator. In many cases, it is desirable for the user to know whether the disposable, limited use, or restricted use device has been exposed to such conditions. Indeed, in many cases, the very purpose of the color change indicator is to determine whether the apparatus in the package has been exposed to certain atmospheric gases such as oxygen. However, there is a need for a sensor with greater user control that allows the user to have greater control over activation of the color change indicator while also allowing for a self-contained sensor that can be applied to a variety of apparatuses.

The present invention relates to a color change sensor comprising a substrate comprising non-atmospheric levels of a gas (i.e., the gas is present in an amount greater or less than the amount of that gas generally present in the atmosphere) wherein the substrate is disposed directly or indirectly on a color change indicator. The gas-containing substrate forms a gas layer on at least a portion of the color change indicator such that it blocks activation of the color change indicator, e.g., it interferes with, inhibits, and/or prevents permeation of atmospheric gases into the color change indicator, or such that it creates an environment that triggers the reaction chemistry of the color change indicator until that environmental state changes. The sensor is directly or indirectly disposed on or used with a disposable, limited, or restricted use apparatus or product including on product packaging. In one embodiment, the sensor further comprises an interface layer, which further controls permeation of atmospheric gases, and may be disposed on the gas-containing substrate or gas layer to assist in controlling the environment present on or in the gas-containing substrate. In one embodiment, the sensor may be activated by destruction or removal of the interface layer. In another embodiment, the sensor further comprises a second substrate on which the color change indicator is directly or indirectly disposed.

In another embodiment, the present invention relates to an apparatus comprising a disposable, limited or restricted use apparatus and a sensor comprising an interface layer, a substrate comprising a gas, and a color change indicator wherein the substrate is disposed on the color change indicator. In one embodiment, the apparatus further includes a second color change indicator, which may be disposed on the sensor.

The substrate for holding or containing the gas may be any suitable substrate that is able to contain or hold gases. For example, any substrate that is porous or contains a matrix or passages in which gaseous substances may become entrapped, held, or otherwise contained would be suitable including, for example, solid substances with permeable matrices or liquids. The porous substrate may act as a sponge such that gases are trapped, contained or otherwise held within the substrate. Examples of appropriate substrates include silicone rubber, urethane foams, or PVC foam. In a preferred embodiment, the gas-containing substrate is surface-modified polymethylmethacrylate (PMMA) or open cell silicone. The substrate comprising the gas may be referred to herein as the "gas-containing substrate" or the "gas layer." The substrate is also referred to as the "gas-containing substrate" or "gas layer" for the embodiments using gas-generating components described further herein.

This substrate includes any suitable gas that would inhibit permeation of atmospheric gases to the color change indicator. Examples of appropriate gases include oxygen, carbon dioxide, nitrogen, argon and ammonia. To inhibit permeation of atmospheric gases to the indicator, the gas is ultimately present in the substrate at non-atmospheric levels, i.e., in concentrations or levels that are greater than or less than the concentration or level of the gas under normal atmospheric conditions. These non-atmospheric levels can be achieved before or after manufacturing of the sensor and/or its components.

For example, to achieve gas concentrations that are greater than atmospheric levels, the substrate can be flooded with the subject gas during manufacturing. For example, the substrate may be placed in a container containing, for example, carbon dioxide or argon. Over time, the gas will permeate the matrix of the substrate and displace atmospheric gas with the subject gas. The subject gas can also be applied to the substrate under pressure to decrease amount of time needed for gas permeation into the matrix. To achieve gas concentrations that are less than atmospheric levels, a gas such as carbon dioxide may be applied to the substrate to displace atmospheric gas with carbon dioxide thereby reducing oxygen concentrations resulting in less than atmospheric oxygen levels. Alternatively, gas may be generated in the gas-containing substrate after initial manufacturing of the substrate as explained further below.

In another embodiment, the substrate can be prepared or formed with one or more gas-generating components. The gas-generating component utilizes chemistry that generates a gas. For example, if the substrate is formed from a urethane foam, a first gas-generating component such as sodium bicarbonate ($NaHCO_3$) in powder form may be added to urethane foam during the manufacturing process (e.g., while the foam is non-solid) such that the powder is incorporated into the substrate. After the substrate has formed or hardened, the substrate (which contains the gas-generating component) may be cut or sliced into strips for further processing into individuals sensors. The strips may be set aside for later processing. While the strips are being laminated or otherwise prepared for processing, a second gas-generating component such as acetic acid ($CH_3COOH$) may be sprayed, painted, or otherwise applied to the substrate containing the first gas-generating component (e.g., sodium bicarbonate). The first and second gas-generating components then react creating or releasing a gas that may then become trapped in the substrate during the manufacturing process. The first and second gas-generating components are components that will react to generate a target gas (such as carbon dioxide). For example, sodium bicarbonate and acetic acid generate carbon dioxide as shown below:

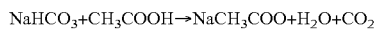
$$NaHCO_3 + CH_3COOH \rightarrow NaCH_3COO + H_2O + CO_2$$

In another example involving gas-generating components, the first gas-generating component (e.g., $NaHCO_3$) is dispersed in the substrate as described above. However, rather than applying the second gas-generating component later during the manufacturing process, the second gas-generating component may be encapsulated e.g., in microspheres or the like, and also added to the substrate such that the first and second gas-generating components are both present, but inactive, in the substrate. The sensor comprising the substrate, which comprises the first and second gas-generating components that are physically separated and inactive, and the color change indicator are assembled. The indicator is exposed to atmospheric conditions and is thus in a state where it can be stored in this environment for extended periods. In this state, the color change indicator is a first color (e.g., blue or purple). Subsequently, during final manufacture or assembly, when the sensor is being applied to a product or when the substrate is applied to the indicator, the manufacturer or assembler may trigger gas generation in the substrate by instigating a reaction between the first and second gas-generating components and triggering generation of gas (e.g., by applying pressure to the substrate, destroying or crushing the microspheres, and releasing a gas-generating component from the microspheres). The presence of the generated gas in the gas-containing substrate or gas layer drives the reaction chemistry in the indicator changing the color of the indicator to a second color (e.g., light grey or bronze and making the sensor ready for end use. Once the gas layer is subsequently removed or destroyed by the end user as described further below, atmospheric gases reach the color change indicator, triggering a color change reaction and returning the indicator to the original condition or first color (e.g., blue). This provides the benefit of allowing the sensor to be assembled separately during manufacturing and assembly.

Examples of the chemistry underlying the color change indicator is described in other patents and applications, for example, as referenced herein and incorporated by reference.

In one embodiment, the gas is dispersed in the substrate. For example, as described above, when the substrate is soaked in the subject gas, the gas becomes dispersed into the matrix or components of the substrate. As another example, the gas is dispersed in the substrate during activation of the gas-generating components. The dispersion may be generally uniform but need not be.

The substrate may itself contain mechanisms to contain the gas therein and/or may be used in conjunction with an interface layer discussed further below. For example, the substrate may contain microspheres, capillaries, or nanotubes that are capable of containing gas. If the substrate itself contains the gas, the substrate includes mechanisms to ensure diffusion in a controlled manner such that the gas layer acts like the gas layer. In a preferred embodiment, the substrate is saturated with the subject gas such as above 60% of the subject gas and, more preferably above 80% of the subject gas thereby minimizing atmospheric gases in the substrate.

The gas layer or gas-containing substrate is disposed directly or indirectly on the color change indicator. The placement of the gas layer or substrate on the color change indicator is oriented such that the gas layer is able to block or inhibit atmospheric gases from contacting the color change indicator, further delaying activation of the indicator. In a preferred embodiment, the gas layer or gas-containing substrate is disposed on top of the color change indicator and covers the entirety of the indicator. The gas-containing substrate or gas layer is any appropriate thickness or dimension sufficient to inhibit or interfere with the ability of atmospheric gases from actuating the color change indicator or penetrating into indicator. For example, the amount of gas in the substrate may vary depending on the rate of gas diffusion from the substrate and/or the rate of gas diffusion from the interface layer.

As described further below, in one embodiment, an interface layer is disposed directly or indirectly on the gas layer or gas-containing substrate and contains the gas present in the layer or substrate. In this embodiment, the interface layer assists in inhibiting the gas from escaping from the gas layer. The interface layer should generally be made from materials having low or very low gas diffusion rates or non-permeable material(s) that may appropriately contain gas in the gas-containing substrate. Examples of materials from which the interface layer may be made include aluminum such as aluminum foil or vacuum-deposited aluminum, polyester films, layered aluminum and plastic, and/or gold or copper-films. The thickness of the interface layer should be any thickness that will appropriately allow containment of the gas in the gas layer. In determining the thickness of the interface layer, consideration should be given to the diffusion rates of materials which form the gas-containing substrate or gas layer and/or the diffusion rates of the materials which form the interface layer. It is noted that different gases also diffuse through materials at different rates. For example, carbon dioxide is a smaller molecule and would diffuse through more quickly. For example, if an interface layer is made from a material or materials with higher gas diffusion rate(s), the thickness of the interface layer may need to be increased or the gas-containing substrate or gas layer may need to be formed of a material which is better able to contain gas to control the exclusion of the atmosphere over time. Alternatively, if an interface layer is made from a material or materials with lower gas diffusion rate(s), the thickness of the interface layer may be decreased and there may be greater flexibility with the materials from which the gas-containing substrate or gas layer is formed. Generally speaking, a thicker interface layer or more interface layers will result in greater gas containment in the gas layer. Conversely, thinner interface layer or less interface layers will allow more gas to escape. Additionally using a material that has a higher or lower diffusion of gas will also shorten or lengthen the time respectively as different gases diffuse through materials at different rates.

The interface layer may be applied to the substrate through any appropriate mechanism. For example, the interface layer may be applied by vacuum deposition, lamination, paint, silk screen or any other appropriate manufacturing means. Adhesives may also be used as described further below.

As discussed further below, the user may activate the sensor including the color change indicator by destroying or removing the interface layer, e.g., by peeling off that layer or puncturing it, or by removing both the interface layer and the gas layer or gas-containing substrate as shown for example in FIG. 6.

The color change indicator may be any appropriate color change indicator including, for example, an indicator that changes color based on changes in carbon dioxide levels (a carbon dioxide-based indicator) or oxygen levels (an oxygen-based indicator). As described above and herein, examples of indicators are described in other patents and patent applications.

The color change indicator uses indicator chemistry to create a color change indication on a product that provides accurate information or a warning to a user of, e.g.: prior use of a single use product or instrument; a reminder that a limited use product has reached its expiration time; or that a product that is restricted for use has been tampered with. The warning indication may be provided by a dye that changes color in a time controlled manner wherein the dye is disposed on the product itself by being either printed on the product or incorporated within the material forming a portion of the product, in this manner dyes are understood to include pigments.

Prior patents and applications co-owned by applicant have dealt with the use of color changeable dyes and color change indicators. For example, U.S. Pat. No. 8,388,131 and U.S. Pat. No. 9,134,285 and U.S. patent application Ser. No. 14/292,246, and their related cases, which are incorporated herein in its entirety by reference, describe color change indicators. U.S. Pat. No. 8,388,131, and its related cases presented, for example, a disposable limited or restricted use apparatus that includes a color changeable portion wherein the time that the color change occurs is controlled so that it coincides to the approximate time of the end of one use of a single use apparatus or to the approximate expiration time for extended but limited or restricted use apparatus. U.S. patent application Ser. No. 14/292,246, for example, describes carbon dioxide sensing color change indicators. U.S. Pat. No. 8,663,998, and its related case, which are incorporated herein in its entirety by reference, presented, e.g., a color changeable dye including a redox indicator to create a color change indication on a product that provides accurate information or a warning to a user of, e.g.: prior use of a single use product or instrument; a reminder that a limited use product has reached its expiration time; or that a product that is restricted for use has been tampered with. The color changeable dye can include a redox indicator, a reduction reaction initiator, an electron donor, an oxygen scavenger, an indicator barrier agent, a thickening agent and an agent to facilitate mixing. The color changeable dye may be, for example, a first color in the presence of oxygen, capable of changing to a second color upon reduction in a substantially oxygen free environment, and capable of changing back to the first color after exposure to oxygen for a period of time corresponding to the intended use time of a disposable or limited use product. U.S. patent application Ser. No. 14/038,586, presented, for example, use protocol indicators having a color changeable dye that changes color after exposure to a particular environment for a defined time. U.S. patent application Ser. No. 14/038,586 is also directed to, for example, an exposure time indicator that uses a color changeable dye or multiple color changeable dyes that change color after exposure to an environment in a sequential manner.

The color changeable dye can be varied in order to change color in response to a variety of different environments for a defined time. In one embodiment, the color change indicator may have a color changeable dye, the dye being translucent or having a first color upon immediate exposure to an environment and for a defined time thereafter and the dye changing color after exposure to the environment for the defined time. The environment can be an oxygen containing environment and the color changeable dye is an oxygen sensing color changeable dye. The environment can also be a carbon dioxide containing environment and the color changeable dye can be a carbon dioxide sensing color changeable dye. The environment can be a carbon dioxide containing environment and the color changeable dye can be an oxygen sensing color changeable dye. Other environments are also appropriate. The environment to which the color changeable dye responds can be chosen based on the environment in which the disposable, limited or restricted use product is intended to be used.

In order to create dyes that change color after exposure to different environment after different periods of time, there are a number of possible approaches. Dyes that have completely different compositions can be used. Variations in the makeup of the dye can be used. Scavenger, such as oxygen scavengers, can be added. Barriers can be also be added. Some examples of color changeable dyes using these approaches to achieve color change at different times or in response to different atmospheres have been addressed in other patents and applications discussed herein, which are hereby incorporated by reference.

In one embodiment, the color change indicator changes color gradually or immediately upon exposure to a particular environment such as atmospheric conditions. In another embodiment, the color change indicator comprises a first indicator color changeable dye, the dye being translucent or having a first color upon immediate exposure to a first environment and the dye changing color after exposure to a second environment; and a second indicator color changeable dye, the dye being translucent or having a first color upon immediate exposure to the second environment and for a defined time thereafter and the dye changing color after exposure to the second environment for the defined time. The first environment can be carbon dioxide or inert gas and the second environment can be atmospheric oxygen.

In one embodiment, the sensor comprising the color changeable indicator is intended for use on or in disposable, limited or restricted use products that can transmit contaminants or disease to a person, cause infection, or decline in quality or potency if reused or used beyond a recommended period of time. In another embodiment, the sensor comprising the color changeable indicator is intended for use on or in packaging for a product for human consumption wherein the product for human consumption can decline in freshness, quality of taste, and/or potency and/or can cause disease if consumed beyond a recommended period of time. The color changeable indicator acts to indicate that a product should no longer be used or consumed.

In another embodiment, the sensor can include color change indicators for use with disposable, limited or restricted use product having multiple use protocols which affect the lifespan of the product. For example, a medical device such as a catheter may have multiple different procedures for which it can be used. The time after which the medical device reaches its expiration may be different depending on the procedure for which it is being used. For example, a connector or adapter may be used in one use protocol in conjunction with a medical device delivering oncology medication where the device should only be used for a single dose, e.g., around six hours. The connector or adapter could alternatively be used in a second use protocol with a catheter that delivers drugs for an infection over a period 96 hours. The connector or adapter could alternatively be used in a third use protocol with a medical device that delivers insulin therapy to a patient over 168 hours. A use protocol indicator utilizes a color changeable dye to indicate the time after which a disposable, limited or restricted use product should no longer be used for a specific use protocol. In such an embodiment, an apparatus with color change indication comprises a disposable, limited or restricted use product and at least one interchangeable use protocol indicator.

The disposable, limited or restricted use product has at least one use protocol or more than one use protocol. Each use protocol may have a defined time after which the disposable, limited or restricted use product should not be used when it has been used for that particular use protocol. For example, a medical device could have one use protocol for which it should not be used after exposure to oxygen for 72 hours, it could have a second use protocol after which it should not be used after exposure to oxygen for 96 hours, a third use protocol after which it should not be used after exposure to oxygen for 168 hours and a fourth use protocol after which it should not be used after a week. As another example, a medical device could have one use protocol for which it should not be used after exposure to oxygen for 6 hours, it could have a second use protocol after which it should not be used after exposure to oxygen for 12 hours, a third use protocol after which it should not be used after exposure to oxygen for 90 hours and a fourth after which it should not be used after 120 hours.

Such use protocol indicators have a color changeable dye that changes color after exposure to a particular environment for a defined time. The defined time corresponds to, for example, the expiration time for a disposable, limited or restricted use product for a particular protocol(s) or the time after which a product should no longer be used or consumed. The use protocol indicators can be interchangeable and can be incorporated into the disposable, limited or restricted use product or be disposed on the disposable, limited or restricted use product. The at least one use protocol indicator can be provided with the disposable, limited or restricted use product.

More specifically, the interchangeable use protocol indicator has a color changeable dye. The color changeable dye is translucent, water white or a first color upon immediate exposure to an environment and for a defined time thereafter. The dye changes color after exposure to the environment for the defined time which corresponds to a time after which the disposable, limited or restricted use product should not be used for a particular use protocol. Where there are multiple use protocols for the disposable, limited or restricted use product there can be multiple interchangeable use protocol indicators. The indicator may be interchangeable such that a single indicator is adapted such that it may be used with multiple different products or different indicators can be used with a single product. The multiple use protocol indicators can have color changeable dyes such that the defined time after which the color changeable dyes change corresponds to the expiration time for the disposable, limited or restricted use product for a particular use protocol. For example, the medical device discussed above with use protocols for which it should not be used after exposure to oxygen for 72 hours, 96 hours and 168 hours could have three use protocol indicators with color changeable dyes that change after exposure to oxygen for 72 hours, 96 hours and 168 hours respectively. The expiration time for a disposable, limited or restricted use product can be the time after which the manufacturer recommends replacement, the time after which the product will decline in quality, potency or effectiveness and/or the time after which the product could be dangerous to use.

In another embodiment, the sensor can include an exposure time indicator that uses a color changeable dye or multiple color changeable dyes that change color after exposure to an environment in a sequential manner. The exposure time indicator creates a spectrum that allows the user to see how much of the product's useful life has been used and how much remains. The exposure time indicator comprises at least one color changeable dye, wherein the at least one color changeable dye is disposed to change color in a sequential manner. The at least one color changeable dye can be translucent or have a first color upon immediate exposure to an environment and change color after exposure to the environment. The exposure time indicator can have a first region of the color changeable dye changes color after a first time, consecutive regions of the color changeable dye change color at increasing time intervals after the first time and a final region changes color after a final defined time. The final defined time can correspond to an expiration time for a disposable, limited or restricted use product. The environment can be an oxygen containing environment and said color changeable dye can be an oxygen sensing color changeable dye. The environment can be a carbon dioxide containing environment and said color changeable dye can be a carbon dioxide sensing color changeable dye. The exposure time indicator can be incorporated into a disposable, limited or restricted use product. For example, the exposure time indicator can be a capillary with the color changeable dye incorporated therein. The exposure time indictor can be disposed on or used with a disposable, limited or restricted use product.

Another embodiment a color change indicator is an exposure time indicator scale that indicates how long a disposable, restricted or limited use product has been exposed to a certain environment and the time remaining before the disposable, restricted or limited use product should no longer be used. In other words, the exposure time indicator reflects a continuum reflecting the time passed and time remaining for the product. Such an apparatus comprises a disposable, limited or restricted use product and an exposure time indicator. The exposure time indicator comprises at least one color changeable dye. The at least one color changeable dye is translucent, milky white or has a first color upon immediate exposure to an environment and the dye changes color after exposure to the environment. The at least one color changeable dye is disposed in such a manner to create a sequential color change that indicates how long the disposable, restricted or limited use product has been exposed to a certain environment and the time remaining before the disposable, restricted or limited use product should no longer be used. The user would not simply know whether a product had reached its expiration date but also how long he or she has until it reaches that date.

One example where this might be useful is a feeding tube that should be replaced after approximately one week. A hospital worker could see the exposure time indicator scale and determine when the feeding should be changed. Another example, of the usefulness of the exposure time indicator could be in determining expiration dates on food. Other examples of products where such an indication could prove useful are cosmetic products, personal hygiene products such as electric toothbrush heads, and home diagnostic kits such as pregnancy tests and ovulation prediction tests. In each of these examples, the exposure time indicator allows the user to better plan for change or removal of the product by indicating how long the user has until the product reaches its expiration time.

The exposure time indicator can have barrier layers over the regions of color changeable dye to achieve the sequential color change.

Such indicators are described, for example, in U.S. application Ser. No. 14/038,586, which is hereby incorporated by reference.

The color changeable dye can be varied in order to change color in response to a variety of different environments for a defined time. In one preferred embodiment, the environment is an oxygen containing environment and the color changeable dye is an oxygen ($O_2$) sensing color changeable dye. In another preferred embodiment, the environment is a carbon dioxide containing environment and the color changeable dye is a carbon dioxide ($CO_2$) sensing color changeable dye. In another preferred embodiment, the indicator with an oxygen or carbon dioxide sensing color changeable dye is contained within a carbon dioxide rich environment and later exposed to an atmospheric oxygen environment. In another preferred embodiment, the indicator with a carbon dioxide sensing color changeable dye is contained within an oxygen rich environment and later exposed to a carbon dioxide rich environment. In another preferred embodiment, the indicator with an oxygen or carbon dioxide sensing color changeable dye is contained within an inert gas environment and later exposed to an atmospheric oxygen or carbon dioxide environment.

The environment to which the color changeable dye responds can be chosen based on a particular use protocol. For example, a medical device could have one use protocol for which it should not be used after exposure to oxygen for 1 hour, it could have a second use protocol after which it should not be used after exposure to oxygen for 8 hours and a third use protocol after which it should not be used after exposure to carbon dioxide for 20 minutes. The color changeable dye for the associated interchangeable use protocol indicators could be selected accordingly such that the color changeable dyes on the three use protocol indicators change after exposure to oxygen for 1 hour, exposure to oxygen for 8 hours and exposure to carbon dioxide for 20 minutes respectively.

The color change indicator may include a first indicator color changeable dye, the dye being translucent or having a first color upon immediate exposure to a first environment (such as carbon dioxide or inert gas) and the dye changing color after exposure to a second environment (such as atmospheric oxygen); and a second indicator color changeable dye the dye being translucent or having a first color upon immediate exposure to the second environment and for a defined time thereafter and the dye changing color after exposure to the second environment for the defined time. As one embodiment, an indicator may include a first indicator dye and a second indicator dye such that the first indicator dye indicates a packaging condition and the second indicator dye is associated with a use protocol. For example, an indicator may include a carbon dioxide sensing dye and an oxygen sensing dye where the indicator is packaged within in a carbon dioxide rich environment which triggers the carbon dioxide sensing dye, indicating that the package is sealed. When the indicator is subsequently removed from the package, the oxygen sensing dye will serve as a use protocol indicator in accordance with the present invention. Moreover, the indicator may be an exposure time indicator as described below.

As mentioned above, in order to create dyes that change color after exposure to different environments after different periods of time there are a number of possible approaches. Dyes that have completely different compositions can be used. Variations in the makeup of the dye can be used. Scavengers, such as oxygen scavengers, can be added. Chemical or physical barriers can be also be added. Some examples of color changeable dyes using these approaches to achieve color change at different times or in response to different atmospheres are discussed below.

Examples of oxygen sensing color changeable dyes with various times of color change are discussed in U.S. Pat. No. 8,388,131 and its related cases (e.g. U.S. Pub. No. 2013/0088683, U.S. application Ser. No. 13/780,050 and U.S. application Ser. No. 13/795,343), which are incorporated herein by reference. For applications where the dye is required to be substantially translucent and wherein the dye is to change color after exposure to atmospheric oxygen after approximately 5-10 minutes, the dye solution may be formed as follows. Approximately 12 grams of glucose is added to 600 cc of distilled de-ionized water. Next, approximately 12 grams of sodium hydroxide is added to the mixture. To this mixture is added 10 cc of a Methylene Blue solution prepared by mixing 0.1 gram of Methylene Blue in 100 cc of ethanol where the ethanol evaporates in the drying process. Thereafter, 60 grams of methyl cellulose is added to the mixture. Alternatively, E414 acacia gum may be substituted for the methyl cellulose. This dye solution will change from translucent to blue in a short amount of time after the packaging is opened and the product on which the dye is disposed is exposed to oxygen. If the color change desired is from substantially translucent to a red color, 10 cc of a Safranine T solution can be substituted for the Methylene Blue solution. The Safranine T solution is prepared by mixing 0.3 grams of Safranine T with 10 ml of ethanol.

In order to delay the time at which the dye changes color upon exposure to oxygen, Iron (II) carbonate can be added to the above dye solution. For example, 0.1 grams of Iron (II) carbonate can be added to a 3 ml quantity of the above dye solution forms a dye that will change color to either blue or red after approximately 9-10 minutes of exposure to atmospheric oxygen. By increasing or decreasing the amount of Iron (II) carbonate the time that it takes for the color change to occur upon exposure to oxygen can be respectively increased or decreased. It is noted that, the addition of the Iron (II) carbonate will change the dye from being substantially translucent to somewhat translucent or a faint, milky white known as "water white" wherein the translucency diminishes as more Iron (II) carbonate is added.

If it is desired that the color change takes substantially longer than 10 minutes at atmospheric oxygen, for example, 12-16 hours at atmospheric oxygen, 0.5 grams of Iron (II) carbonate is added to a 3 ml quantity of the dye solution instead of 0.1 grams of Iron (II) carbonate. It is noted that the Iron (II) carbonate acts as an oxygen scavenger in the dye solution that preferentially absorbs oxygen, converting to Iron (III) carbonate. When the Iron (II) carbonate is completely converted to Iron (III) carbonate, the oxygen in the environment reacts with the color changeable dye so that the dye changes to blue or red and becomes visible.

In order to prevent the dye from changing color until an even longer time has passed, wax can be added to the dye solution. To provide a color change indication on a product after approximately 1500 hours at atmospheric oxygen, the oxygen diffusion rate through the dye solution can be lowered or decreased by the addition of wax as follows. Specifically, when 0.3 cc of beeswax is added to a 3 ml quantity of the dye described above, the color change is delayed by approximately ten hours at atmospheric oxygen for a volume of dye of 0.01 mm3. This amount of dye can be used in an area of approximately 2 mm in height and 20 mm long on a product. With the addition of 0.6 cc beeswax to the dye solution, the color change can be delayed to approximately 100 hours at atmospheric oxygen. To further extend the time that it takes for the color change to approximately 1500 hours at atmospheric oxygen, 0.7 grams of Iron (II) carbonate can be added to the dye solution and wax mixture.

Examples of color changeable dyes including dyes incorporating redox indicators are discussed in U.S. Pat. No. 8,663,998, which is incorporated herein by reference. That application discusses a color changeable dye of the that may include a redox indicator, a reduction reaction initiator, an electron donor, oxygen scavenger, an indicator barrier agent, an agent to facilitate mixing and a thickening agent wherein the color changeable dye changes to a warning color after exposure to oxygen for a predetermined period. Potential redox indicators discussed in that patent include indigo tetrasulfonate, phenosafranine, methylene blue, diphenylamine, 4'-ethoxy-2,4-diaminoazobenzene, diphenylamine sulfonic acid, diphenylbenzidine sulfonic acid, tris(2,2'-bipyridine)iron, tris(1,10-phenanthroline) iron (ferrion), tris (5-nitro-1,10-phenanthroline) iron and tris(2,2'-bipyridine) ruthenium. The preferred redox indicator discussed in that application is indigo tetrasulfonate (ITS).

A reduction reaction initiator initiates the reduction of the redox indicator. An example of a reduction reaction initiator is titanium dioxide. An electron donor donates electrons to the reduction reaction initiator to allow for reduction of the redox indicator. Examples of electron donors include glycerol and sugars. In a preferred embodiment the reduction reaction initiator is titanium dioxide and the electron donor is glycerol.

Oxygen scavengers act to delay the oxidization of the redox indicator by reacting with oxygen before allowing the oxygen to react with the redox indicator. Examples of oxygen scavengers include sodium bisulfate, ascorbic acid, iron (II) carbonate. Preferred oxygen scavengers are sodium bisulfate, ascorbic acid and iron (II) carbonate.

An example of a color changeable dye that reacts based on carbon dioxide levels in its environment could include a carbon dioxide reactive dye such as cresol red (CR, o-cresolsulfonephthalein) example formulation of 1:cresol red, 20: glycerol, 3: 10M KOH (aq), Texas red hydrazide (THR), bromothymol blue (BTB, hydroxy triarylmethane), or m-cresol purple (MCP, hydroxyl triarylmethane). This carbon dioxide reactive dye could be mixed with a solvent such as alcohol, methanol or acetone. Bentonite nanoclay or diatomaceous earth could be added to give the color changeable dye desirable physical properties.

Examples of carbon dioxide based color change indicators are described in U.S. application Ser. No. 14/292,246, which is hereby incorporated by reference.

A color changeable dye may include a carbon dioxide status indicator, a solvent, a polymer wherein the carbon dioxide status indicator is dispersed, an optional plasticizer, and an optional agent to facilitate mixing wherein the color changeable dye changes to a warning color after exposure to a change in carbon dioxide environment for a predetermined period. A carbon dioxide status indicator is a compound that changes color because it is exposed to a change in carbon dioxide environment, i.e., the additional presence or absence of carbon dioxide either before or after the color change is what triggers the change in color, and is used to indicate a change in the carbon dioxide environment. Examples of carbon dioxide status indicators include Cresol Red, Texas Red Hydrazine, Bromothymol Blue, M-Cresol Purple, Phenol Red, Congo Red and Natural Red.

The color changeable dye can be a first color in the presence of a higher than atmospheric carbon dioxide environment, and can be capable of changing to a second color after exposure to atmospheric conditions for a period of time corresponding to the intended use time of a restricted, disposable or limited use product. In one example, the period of time is less than about 60 minutes. In another example, the period of time is between about 1 and about 168 hours.

In one embodiment, the carbon dioxide status indicator is a pH status indicator. A pH status indicator is a compound that changes color when exposed to a change in pH and is used to indicate a change in environment. A pH status indicator can be incorporated into the present color changeable dye to allow for a color change upon exposure to a change in carbon dioxide environment. That change could be either an increase or a decrease in the carbon dioxide concentration of the environment. Examples of possible pH status indicators and their corresponding colors are shown below in Table 1.

TABLE 1

| pH Status Indicator | Acid or Low pH Color | pH Transition Range | Base or High pH Color |
|---|---|---|---|
| Cresol Red (CR, o-Cresolsulfonephthalein) | yellow | 7.2-8.8 | reddish-purple |
| Bromothymol blue (BTB, Hydroxy triarylmethane) | yellow | 6.0-7.6 | blue |
| Congo red (sodium salt of benzidinediazo-bis-1-naphthylamine-4-sulfonic acid) | blue-violet | 3.0-5.0 | red |
| Phenol red (PR, phenolsulfonphthalein) | yellow | 6.4-8.0 | red |
| Neutral red (NR, toluoylene red) | red | 6.8-8.0 | yellow |

Texas Red or m-Cresol Purple could also be used. The acid low pH color for these dyes is a light yellow. Texas Red transitions from yellow to red at about 4% $CO_2$. m-Cresol purple transitions from yellow to purple at approx. 2% $CO_2$. It is understood that other status indicators could be substituted in the color changeable dye of the present application. Preferred pH status indicators for use in the present solution are Cresol Red, m-Cresol Purple and Phenol Red.

A pH status indicator is a halochromic chemical compound that is added in small amounts to a solution so that the pH of the solution can be determined visually. A pH status indicator is a chemical detector for hydronium ions ($H_3O^+$) or hydrogen ions ($H^+$) in the Arrhenius model. Normally, the indicator causes the color of the solution to change depending on the pH. The reactions of pH indicators can be simplified as follows:

H Ind(Acid or Low pH Color)+$H_2O$↔$H_3O^+$+Ind⁻
(Base or High pH Color)

As an example of how the pH status indicators function in different carbon dioxide environments, for Cresol Red the acid or low pH color is yellow and the base or high pH color is reddish purple. When the Cresol Red is in a carbon dioxide rich environment, for example a pure 100% carbon dioxide environment, it will be in the H Ind form which is the acid or low pH color of yellow. When placed in a lower carbon dioxide environment, for example an atmospheric environment with approximately 0.0397% carbon dioxide, the Cresol Red changes to its Ind⁻ form which is the base or high pH color of reddish purple. This would apply similarly to the other pH status indicators in the chart above with their respective high and low pH colors.

A benefit is that the pH status indicator can be incorporated into the color changeable dye in its acid or low pH form (the yellow form in the case of Cresol Red) in a carbon dioxide rich environment. The product can then subsequently be packaged to provide a sterile environment for the product. The internal atmosphere of the package can be pure carbon dioxide (approximately 100% carbon dioxide) or any other amount of carbon dioxide higher than the amount of carbon dioxide in the atmosphere, e.g. 10%, 20%, 30%, 40%, 50%, 60%, 70%, 80%, 90% carbon dioxide.

When the color change indicator is actuated and the indicator is exposed to atmospheric conditions with a lower carbon dioxide content (approximately 0.0397% carbon dioxide), the dye disposed on the product will change from its acid or low PH state (yellow for Cresol Red) to its base or high pH state (reddish purple for Cresol Red) after a period of time that is controlled by the composition of the dye as discussed in detail below, and that is selected to correspond to the typical time for a single use of a product in the case of single use products or that corresponds to the expiration time of the product. The time at which the dye changes color can also be selected so as to indicate that the product may have been tampered with.

For single use disposable products the dye may be required to be substantially translucent in its high carbon dioxide environment and change color after exposure to atmospheric conditions after a number of minutes, a number of hours, or a week. For example, the color changeable dye that changes after exposure to atmospheric conditions for a number of minutes could be used with a disposable syringe that is intended for a single use that takes less than 10 minutes.

A polymer may act to delay the change of the indicator by forming a physical or chemical barrier around it. Examples of polymers in which the indicator can be dispersed in include polyvinyl alcohol (PVA), hydroxyethyl cellulose (HEC), hydroxypropyl cellulose (HPC), polyvinyl butyral (PVB), polyvinyl chloride (PVC), polyethylene terephthalate (PET), or polymers made from vinylidene chloride (especially polyvinylidene chloride or PVDC), along with other monomers, e.g. Saran®.

The color changeable dye may contain a solvent. The solvent can be added to the color changeable dye to dissolve the indicator or other dye components. Preferred solvents include acetone, alcohol, ethanol, methanol and water.

A benefit of the color changeable dye, as discussed in other patents and applications, is that the color change can be delayed so that it does not begin immediately upon exposure to an atmospheric environment but rather at some predetermined time based on recommended use of the product. For example, the dye could turn color (reddish purple for Cresol Red) after a period of days for a product that is intended to be used for a certain number of days after opening or actuation. As another example, the dye could turn color (reddish purple for Cresol Red) after minutes for a product that should be used within minutes of opening or actuation. In order to delay the color change of the dye upon exposure a polymer wherein the indicator is dispersed can be included.

It is understood that one can vary particular aspects or volumes of the components of the color changeable dye in order to vary the timing of the color change after exposure to oxygen between a number of minutes, a number of hours or a week. For example, one could vary the type, number or amount of polymer used in the color changeable dye to vary the timing of the color change. Variations in the molecular weight of the polymer could also be used to vary the timing of the color change.

Other agents can be added to the color changeable dye in order to give the dye physical properties that make it usable for its intended purpose. Barriers are discussed herein. Another example is a thickening agent can be added to the dye to give it a workable consistency. A preferred thickening agent is 2-hydroxyethyl cellulose. As another example of an agent that gives the dye physical properties that make it usable for its intended purpose, an agent to facilitate mixing lessens the tacky nature of the redox indicator and creates microspheres to help the hygroscopic glycerol mix with an aqueous solvent and form a usable solution. Examples of agents to facilitate mixing include bentonite nanoclay, glass microspheres, diatomaceous earth and cellulose acetate. A preferred agent to facilitate mixing is bentonite nanoclay.

Other agents that can be added to give the dye physical properties that make it usable for its intended purpose include, for example, a plasticizer to give it plastic or moldable qualities. A preferred plasticizer is glycerol.

In one embodiment, the color change indicator or dye is disposed directly or indirectly on a substrate that, e.g., facilitates manufacturing and placement of the color changing sensor on or with the disposable, limited use, or restricted use product. Examples of possible substrates include a sintered material comprised of plastic, metal or other such material, a hydroxyethyl-methacrylate substrate such as that used for hydrophilic contact lenses (daily wear disposables) or a sponge that has been extruded into a filament or a strip and then dipped into the color changeable dye.

The substrate with the dye thereon could then be laminated or encapsulated under a controlled atmosphere (e.g., inclusion of or exclusion of carbon dioxide) between layers of plastic material such as Poly(vinyl chloride), (PVC), Polyethylene terephthalate (PET), or Saran having very low atmospheric diffusion rates; thus forming an indicator strip. Additionally an adhesive back could be applied to the strip to form a sticker type indicator. Under a controlled atmosphere, the top of the indicator strip would be trimmed or cut off, thus presenting a small atmospheric aperture to the extruded filament or strip. The indicator strip could then be placed onto, within or around any device or into a package or incorporated into a sensor as described herein. The package would preferably be flood filled with, e.g., carbon dioxide. The package would be closed/sealed.

The color change indicator and/or or color changeable dye can be applied to the product using a number of methods known in the present art. For example, the solution can be applied to the product by printing, painting, spraying, deposition, dipping, flowing or another method known in the art.

For example, for a carbon dioxide indicator, the dye may be applied in its acid or low pH form (yellow for Cresol Red) and dries quickly after being placed on the product. The application of the dye is done in an environment with higher than atmospheric carbon dioxide content. After the dye is dry, an adhesive backed carbon dioxide infused foam layer is placed over the indicator. The product can then be sterilized with any common, low temperature sterilization technique and sealed container or package with an internal atmosphere with higher than atmospheric carbon dioxide content.

The indication timing control could be adjusted by adjusting the rate of gas diffusion out of the indicator substrate, by decreasing the diameter of the aperture thus lengthening the time of the indication, or by making the strip assembly longer. A combination of adjustments such as length and aperture could also be used.

In one embodiment, a chemical or physical barrier may be used to delay activation of the color change indicator. Examples of barriers are described in U.S. patent application Ser. Nos. 14/038,586 and 14/292,246, which are incorporated herein. Examples of barriers include waxes that form a physical barrier around the color change indicator and/or its components. The polymer poly(diallydimethylammonium chloride) also known as PDADMA is an example and may act to create a nanoreactor in the color changeable dye.

Barriers can also be used to achieve the extended sequential color change of the color change indicator. Physical polymer barriers can be applied over the color changeable dye to create color change at different times, e.g., in a stepwise fashion to create a sequential color change. A color changeable dye such as those described above can be disposed onto a substrate, such as a paper indicator strip. Polymer sheets, such as polypropylene, are then disposed on top of the color changeable dye. The polymeric sheets in this can be disposed with different number of sheets depending on when color change is desired, e.g., with no sheets on the first region, one sheet on a second region, two sheets on a third region, three sheets on a fourth region and so on. Single sheets of increasing thickness can also be used.

Figure 9:
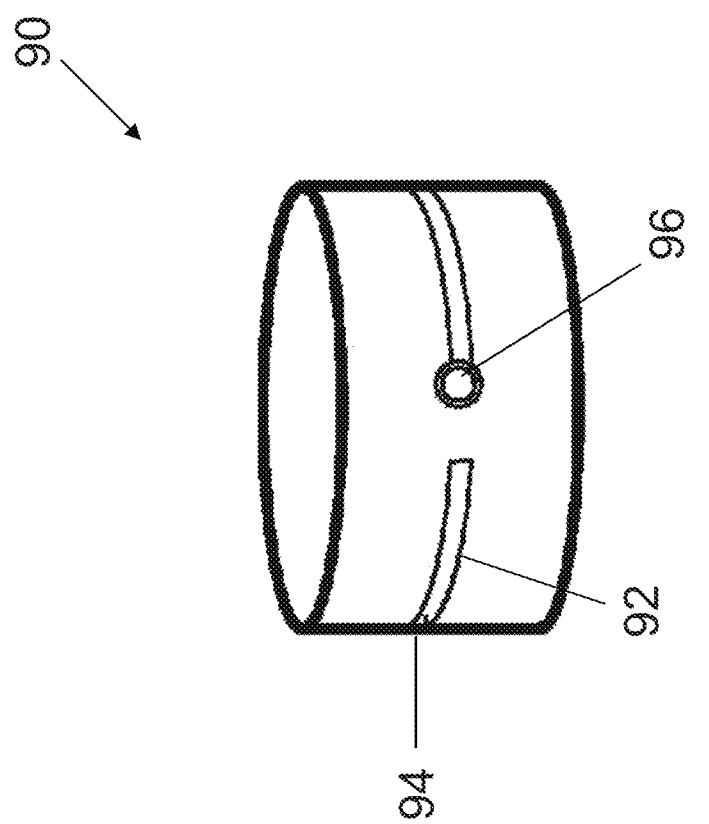
FIG. 9 is a schematic drawing of one embodiment of the present invention showing a capillary containing a color change sensor.

As another example, the sensor could be presented in the form of a capillary with the color change indicator and dye incorporated therein. FIG. 9 is a schematic drawing showing an interchangeable component with a capillary containing a color changing sensor.

Figure 3A:
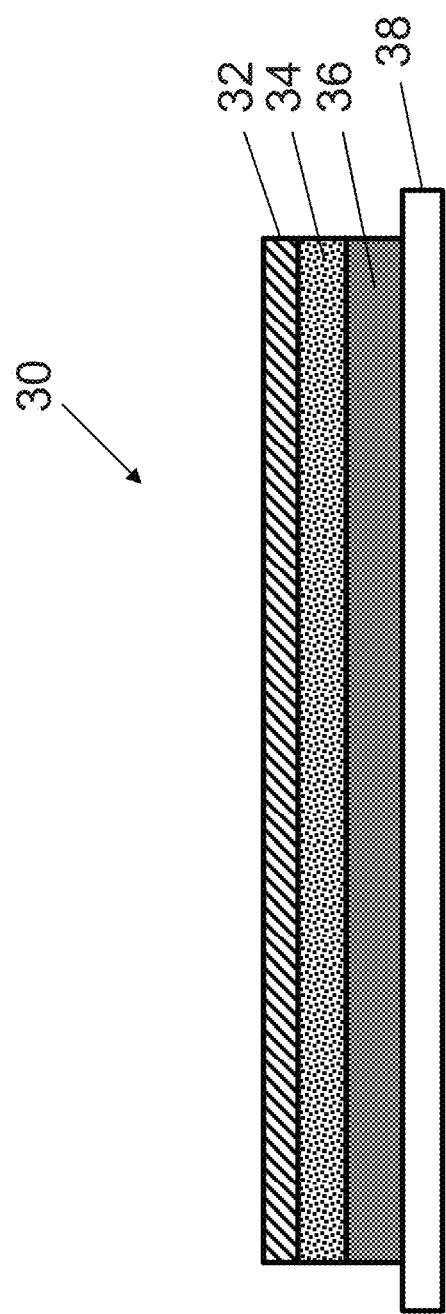
FIG. 3A is an illustration of one embodiment of the present invention showing a color change sensor comprising an interface layer, a gas layer or gas-containing substrate, a color change indicator, and a second substrate.

FIG. 3A is an illustration of one embodiment of the present invention. As shown in FIG. 3A, a color change sensor 30 comprises an interface layer 32, a gas layer or gas-containing substrate 34, a color change indicator 36, and substrate 38. The color change indicator 36 is directly disposed on substrate 38. The gas layer or gas-containing substrate 34 is directly disposed on the color change indicator 36. The gas layer or gas-containing substrate 34 contains non-atmospheric levels of a gas such as carbon dioxide. Alternatively, the gas layer or gas-containing substrate 34 contains a gas-generating component or components that generate a gas. When subject gas is present in the gas layer, the gas layer interferes with atmospheric gas that triggers the color change chemistry in the color change indicator 36. Disposed on the gas layer or gas-containing substrate 34 is an interface layer 32. The interface layer 32 contains the gas in the gas layer or gas-containing substrate 34. While the embodiment of FIG. 3A depicts the interface layer 32 disposed on top of the substrate 34 comprising the gas, the user can select any method to contain the gas in the gas layer including those described herein.

FIG. 3B depicts another embodiment of the present invention. As shown in FIG. 3B, a color change sensor 30 comprises an interface layer 32, a gas layer or gas-containing substrate 34, a color change indicator 36, and substrate 38. The color change indicator 36 is directly disposed on substrate 38. The gas layer or gas-containing substrate 34 is directly disposed on the color change indicator 36. Disposed on the gas layer or gas-containing substrate 34 is an interface layer 32. The interface layer 32 contains the gas in the gas layer or gas-containing substrate 34. The embodiment of FIG. 3B depicts the interface layer 32 disposed on top of the substrate 34 and also disposed on the color change indicator 36. Placement of the interface layer depends on the configuration of the sensor and its components.

FIG. 4 depicts another embodiment of the present invention. FIG. 4 depicts a color change sensor 40 comprising a gas layer or gas-containing substrate 42 disposed on a color change indicator 44. The gas layer or gas-containing substrate 42 is disposed on the color change indicator 44 in such a way that the gas layer 42 further slows atmospheric gases from reaching the color change indicator. It is noted that that the gas layer or gas-containing substrate 42 may be disposed on the indicator 44 in a way that surrounds the indicator. Placement of the gas layer may depend on the configuration of the sensor and its components. The user may activate the sensor 40 by removing or puncturing the gas layer 42 allowing the gas in the substrate to escape and atmospheric gases to directly access the color change indicator 44. The sensor 40 may be disposed directly on or used with a limited, restricted use, or disposable apparatus, which itself may be contained in packaging that is flood-filled with non-atmospheric gases.

In one example, a sensor with a gas layer and carbon dioxide indicator could be used. In this example, the sensor comprises a color change indicator that is a carbon dioxide-based indicator and a gas layer comprising greater than atmospheric levels of carbon dioxide. A substrate such as urethane foam is soaked in carbon dioxide gas. The gas-containing substrate is then applied to a carbon-dioxide based color change indicator, which has previously been silk screened onto a non-diffusive substrate. A low diffusive interface layer is then applied on top covering the entire assembly thus forming a laminated structure. The sensor is then applied to a disposable, limited use, or restricted use product such as a catheter or a vascular access device. Before the sensor is activated, and as assembled, the carbon dioxide based color change indicator will have a first color, for example, a brightly-colored indication as it is in the presence of greater than atmospheric levels of carbon dioxide. This is because the excess carbon dioxide gas in the gas layer triggers the reaction chemistry in the indicator causing a reduction reaction. This first color may be blocked from the user's view due to the interface layer which may obscure the color change indicator. When the user removes the interface layer and gas layer, the carbon dioxide gas in the gas layer diffuses out of that layer. This causes the indicator to change to a second color at a predetermined time. The time is determined by the chemistry of the color change indicator and may correlate with a time after which the disposable, limited use, or restricted use product should no longer be used. Thus, the exposed indicator changes from a first color (e.g., grey or bronze colored shade) to a second color (e.g., bright blue or purple) at the predetermined time. Alternatively, the indicator may be an exposure time indicator with various stepped regions that allow for gradual color change at different predetermined times. This color change occurs because the excess amount of carbon dioxide in the gas layer is no longer present, which triggers reversal of the reduction reaction.

In another example, the color change indicator is an oxygen-based indicator and the gas layer comprises greater than atmospheric levels of carbon dioxide. An oxygen-based indicator such as those described in prior patents and applications is applied to a substrate as described in the preceding paragraph. A substrate is soaked in carbon dioxide and applied to the indicator as described in the preceding paragraph. The carbon dioxide layer has at least 50% carbon dioxide to ensure oxygen levels in the gas layer or gas-containing substrate are less than atmospheric. The color change indicator is a first color in the presence of less than atmospheric levels of oxygen. The excess carbon dioxide in the gas layer inhibits atmospheric oxygen from reaching the oxygen based color change indicator and inhibits oxygen from initiating an oxidation reaction. However, after the gas layer is removed, the indicator is exposed to atmospheric oxygen and the oxidation reaction is initiated. This causes the oxygen based indicator to gradually change to a second color at the defined time.

To facilitate adhesion of the various layers, an adhesive can be applied between the various layers, e.g., between the interface layer and the gas layer, between the gas layer and the color change indicator, and/or between the color change indicator and the substrate to which it may be held. Examples of suitable adhesives include polyurethane, polyol, and/or acrylic.

Figure 5:
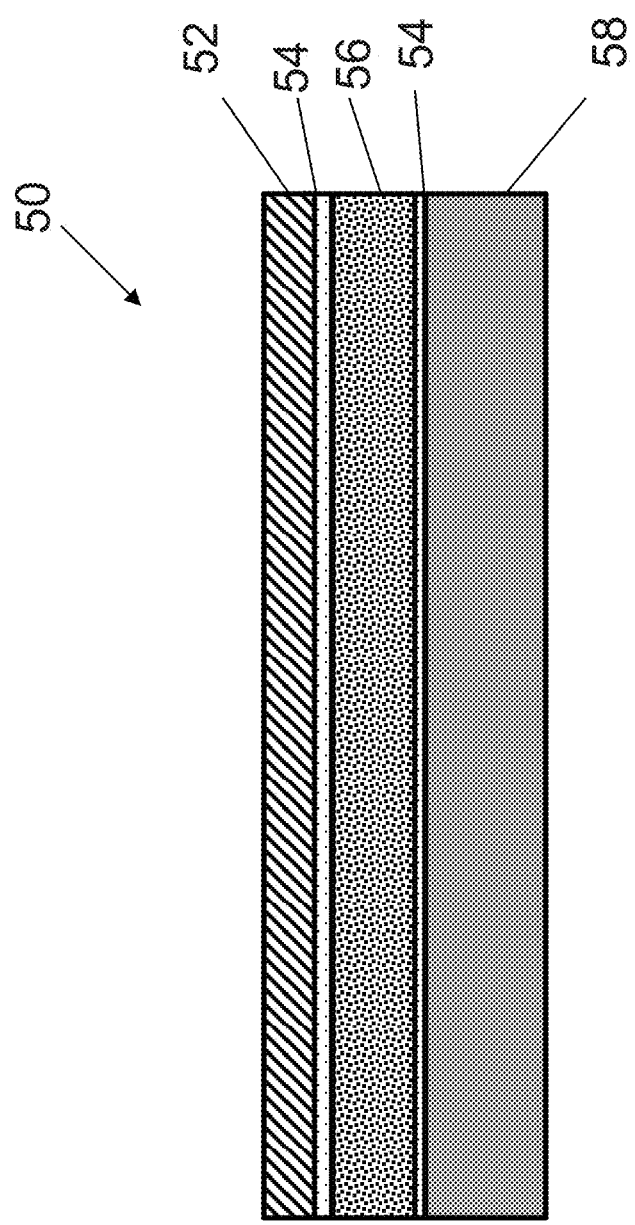
FIG. 5 is an illustration of another embodiment of the present invention showing a color change sensor comprising an interface layer, a gas layer or gas-containing substrate, and a color change indicator with adhesive materials between the interface layer and the gas layer and between the gas layer and the color change indicator.

FIG. 5 depicts another embodiment of the present invention showing a color change sensor 50 comprising an interface layer 52, a gas layer or gas-containing substrate 56, and a color change indicator 58. The interface layer 52 is disposed on the gas layer or gas-containing substrate 56, which is disposed on the color change indicator 58. Adhesive materials 54 between the interface layer 52 and gas layer 56 and between the color change indicator 58 and gas layer 56 allow the layers to adhere together. Alternatively, as described above, each layer may be applied to the underlying or surrounding layer via processes known in the art such as vacuum deposition, silk screening, painting and other known methods.

It is noted that the sensor may be applied in any appropriate way to the disposable, limited use, or restricted use product or its associated packaging including, for example, by use of adhesives and other known methods. As described above, components of the sensor can be supplied for later manufacturing or assembly.

One advantage of the present invention is that the user may activate or actuate the sensor by removing, breaking or otherwise dislodging or destroying the gas layer or gas-containing substrate thereby exposing the color change indicator to atmospheric conditions and/or allowing the gas in the gas layer to escape. In one preferred embodiment, the user actuates the sensor by puncturing or peeling off the gas-containing substrate exposing the color change indicator. Removing or destroying the gas-containing substrate releases the gas contained within the substrate and may allow for controlled exposure of the indicator. In another embodiment, the user actuates the sensor by removing, breaking or otherwise dislodging or destroying the interface layer, with or without the gas-containing substrate, such as by peeling off the interface layer. This also exposes the color change indicator as atmospheric gas is able to permeate toward the gas layer and/or indicator. Peel activation is particularly preferred in the context of a color change sensor that is presented in the form of a label such as shown in FIG. 6.

Figure 6:
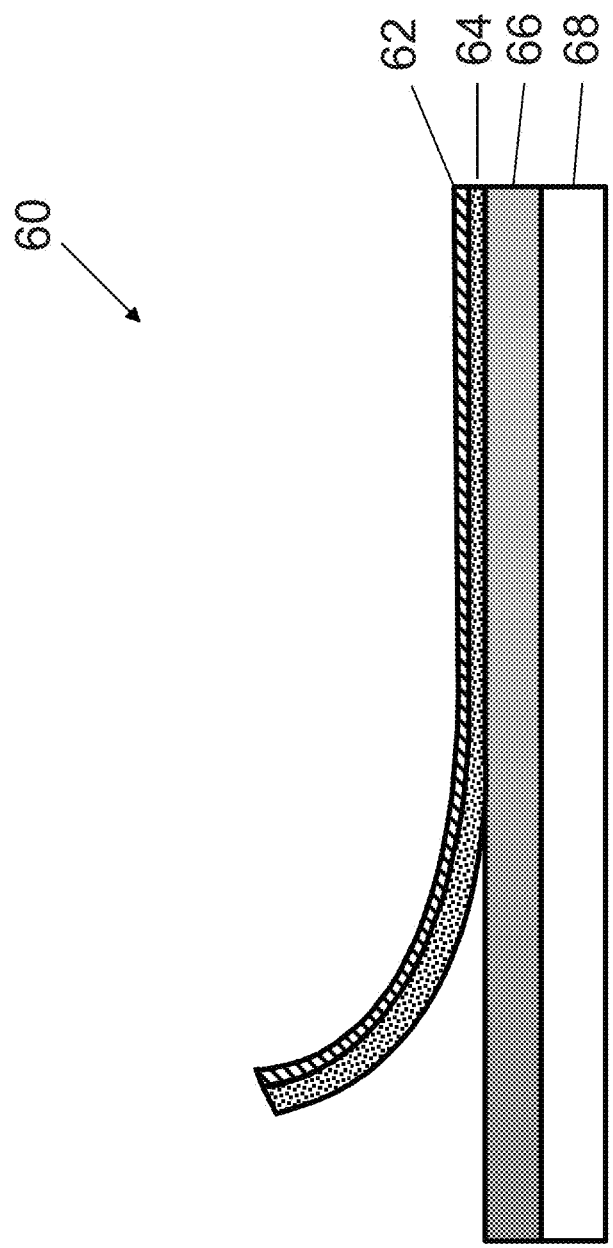
FIG. 6 is a color illustration of a sensor of the type shown in FIG. 3A wherein the color change indicator is being activated by removal of the gas layer and interface layer.

FIG. 6 is an illustration of one embodiment of the present invention. FIG. 6 depicts a color change sensor 60, for example of the type shown in FIG. 4, that comprises an interface layer 62, a gas layer or gas-containing substrate 64, a color change indicator 66, and a substrate 68 on which the indicator is disposed. FIG. 6 depicts peel activation. In other words, FIG. 6 depicts how a user may activate the color change sensor by, for example, detaching or peeling the interface layer 62 and gas layer or gas-containing substrate 64 from the color change indicator 46. As explained above, the gas layer 64 may be attached to the color indicator 66 with an adhesive that allows for easy detachment or peeling by the user. By removing the interface layer 62 and gas layer 64, the color change indicator 66 is exposed to atmospheric conditions or another environment. As shown by the plurality of colors in FIG. 6, color change indicator 66 changes color in a slow and controllable manner.

Figure 7:
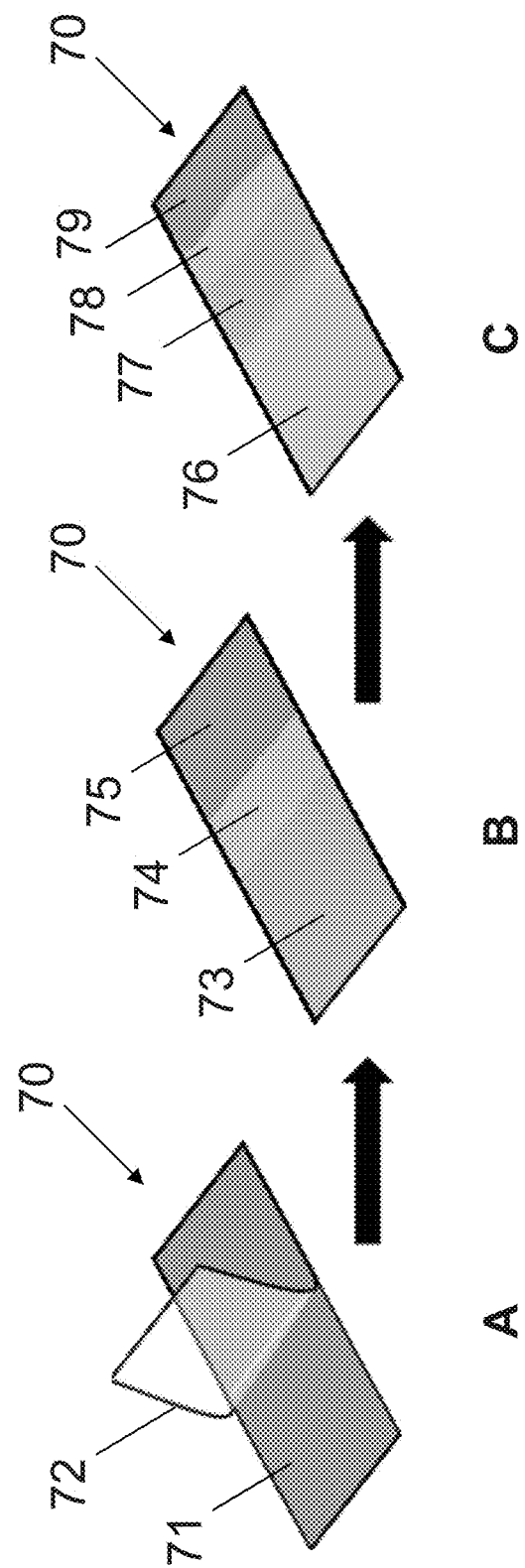
FIG. 7 is a color illustration of a color change sensor that is being activated or has been activated showing gradual activation after time A, after time B, and after time C.

FIG. 7 is an illustration of one embodiment of the color change sensor 70 of the present invention and depicts peel activation. FIG. 7 shows the sensor 70 showing gradual activation after time A, after time B, and after time C after the layer 72 has been removed. At time A, the layer 72 is being removed exposing a portion or region of the color change indicator. At time A, the indicator has a first color (blue) shown at 71. At time B, the layer 72 has been completely removed and the indicator has gradually changed to a plurality of colors 73, 74, 75. At time B, the indicator has three color changing regions: an initially exposed region 73 of the indicator has a second color (green) and a second 74 and third region 75 of the indicator have a third color (light blue) and the first color (blue), respectively. At time C, color change continues to take place with the initially exposed region 76 having a fourth color (yellow), the second region 77 now having the second color (green), and the third region now having the third color (light blue) 78 and first color (blue) 79.

The color changing sensor can be provided in a number of different ways. In one embodiment, the sensor can be incorporated into the disposable, limited or restricted use product itself. A sensor that is incorporated into a product can be combined, inserted, joined or otherwise fixed into the disposable, limited or restricted use product itself (e.g., by the manufacturer or the end user). In another embodiment, the sensor can be disposed on the disposable, limited or restricted use product. A sensor may be attached, affixed, adhered or otherwise fixed or disposed directly upon the disposable, limited or restricted use product itself (e.g., by the manufacturer or the end user). In another embodiment, the sensor can also be indirectly disposed on the disposable, limited or restricted use product. For example, the sensor can be disposed on an adhesive label or other substrate on the disposable, limited or restricted use product. In yet another embodiment, the sensor can be provided with but separate from the disposable, limited or restricted use product. Alternatively, the sensor can be provided independently such that a user can use the indicator on a variety of different products. The sensor may display a message on the disposable, limited, or restricted use product so that, when the color change occurs, the message, such as the word "USED," becomes visible to the user.

In yet another embodiment, the sensor can provided with but separate from the disposable, limited or restricted use product. In one embodiment, more than one sensor can be provided allowing a user to select an appropriate sensor for an intended use. For example, different sensors could be provided in the packaging for a disposable, restricted or limited use medical device such as a feeding tube, catheter or connectors. The multiple sensors could be provided in the form of adhesive use protocol indicators that can be disposed on the medical device or a component such as plastic component that can be snapped into the medical device. The user could then select the sensor associated with the use protocol for which he or she intends to use the medical device. That sensor could be incorporated into the medical device or disposed on the medical device. The medical device could then be used in the intended environment. For example, the color changeable dye on the use protocol indicator would then change color at the defined time after which the medical device should no longer be used for that particular use protocol. As another example, multiple adhesive sensors could be included in a package with a medication that has a different shelf life based on different uses. The user could then select the adhesive use protocol indicator appropriate for his or her intended use and attach it to the packaging for the medication. The sensor would then change color at the time after which the medication should no longer be used for that particular intended use.

In yet another embodiment, more than one sensor or components of the sensors are included in a kit. For example, the kit could include at least one substrate comprising a gas and at least one color change indicator for assembly by the end user or the kit could include multiple assembled sensors with the gas-containing substrate disposed on the color change indicator. The user than selects the appropriate sensor for the appropriate use. In one embodiment, the kit is provided with a substrate comprising gas-generating component(s) and/or separate gas-generating components so that the user can initiate gas generation and assemble the sensor. The sensors may be provided with or without a disposable, limited or restricted use product. They can be appropriate for use with numerous disposable, limited or restricted use products.

In yet another embodiment of the present invention, a kit comprises at least one sensor comprising a gas layer and at least one color change indicator. Alternatively the kit may comprise at least one substrate comprising non-atmospheric levels of a gas and at least one color change indicator. In this way, the user may assembly at least one color change sensor to satisfy his or her particular needs. For example, the kit may comprise more than one use protocol indicator having different defined times. The kit further may include a disposable, limited or restricted use product. The use protocol indicators can be adhesive use protocol indicators.

For example, a kit of adhesive interchangeable sensors could be provided with different color change times, e.g., 1 day, 3 days, 5 days, one week, etc. The user could then apply the sensors indicators on products, e.g., food items in a refrigerator based on the best buy date. In another example, the sensors could be elastic loops, such as rubber bands, that could be wrapped around various products. As discussed above, the sensors can be incorporated into the disposable, limited or restricted use product. The sensor can be a portion of the disposable, limited or restricted use product having an appearance indicative of the use protocol for which the disposable, limited or restricted use product is intended. For example, the use protocol indicator(s) can be a portion of the disposable, limited or restricted use product having a particular color associated with a particular use protocol.

In yet another embodiment of the present invention, there is a method of using an apparatus with color change indication comprising a color changeable sensor comprising a gas layer and a color change indicator. As described herein, the sensor may include other components such as an interface layer, a barrier or additional substrates and may be used with a disposable, limited or restricted use product. Also described herein has been a method of assembling a sensor comprising a substrate containing a gas and a color change indicator in conjunction with additional components.

As one example, the color change sensor could be used with a disposable medical device that is intended for use in a surgery that takes hours to complete. The medical has the sensor of the present invention disposed thereon in an area that will be clearly visible to the surgeon when the dye changes color. Before the surgery, the device could be removed from its packaging, if any, and placed on a preparatory table for later use by the physician. Later, at the outset of the surgery, the surgeon may activate the color change sensor by removing the interface layer and gas layer exposing the color change indicator. After activation, a warning message may appear on the medical device to inform the surgeon that the device has been "USED" wherein the color change occurs after a certain number of hours after the sensor is activated. In this way, the surgeon is warned that the scalpel should not be inadvertently used again but should be disposed of. The present invention allows for flexibility allowing the surgeon to control activation or actuation of the color change sensor.

Figure 8:
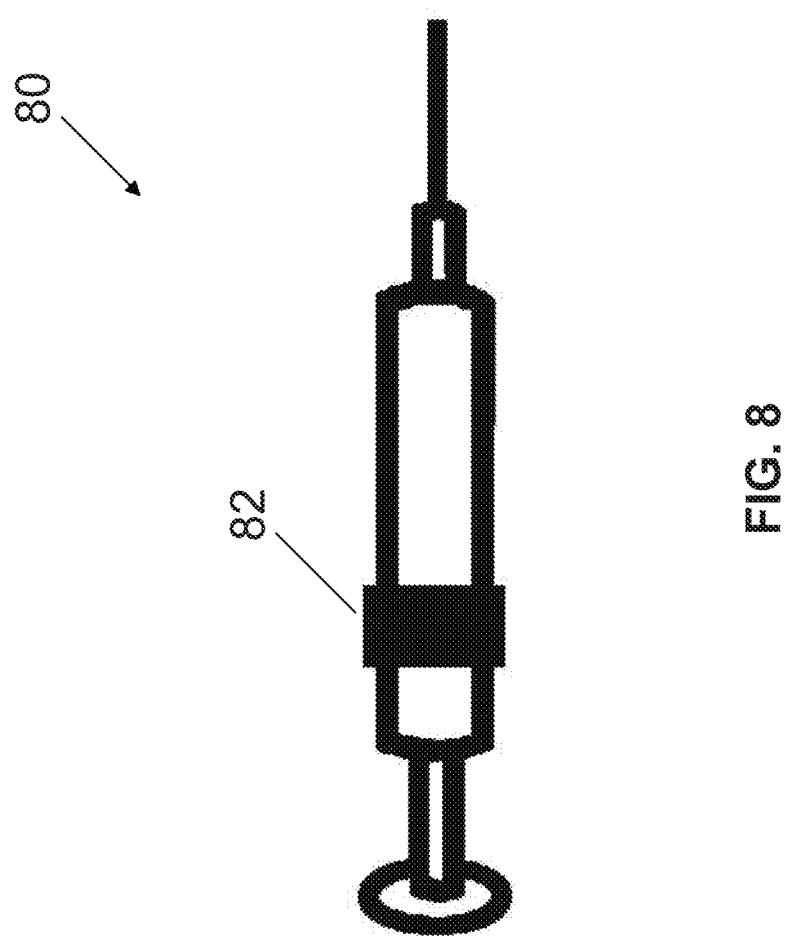
FIG. 8 is a schematic drawing of one embodiment of the present invention showing a medical device having an interchangeable sensor incorporated therein.

FIG. 8 is an illustration of a syringe 80 with a removable and interchangeable color change sensor 82 disposed thereon.

FIG. 9 is a schematic drawing showing an interchangeable component 90 with a capillary 92 containing a color change indicator 94 that comprises both a color change indicator and gas layer of the present invention. The capillary 92 is incorporated into the interchangeable component 90. The capillary 92 can be a metal or plastic material and protects the color change indicator from atmospheric conditions or other environmental conditions. The capillary 92 has an aperture 96 that may comprise a gas layer as well as an optional interface layer depending on the construction of the gas layer. The user actuates the sensor by depressing the aperture 96 disrupting or otherwise destroying the gas layer and the optional interface layer. Once actuated, this allows the environmental conditions to access the color change indicator 94 within the capillary triggering the color change reaction. This controls the manner in which the environment conditions contact the color change indicator 94. Additional barrier materials may be incorporated into the capillary to further delay the color change of the dye.

The color changing sensor may have a variety of uses and applications. As yet another example, the color change sensor could be configured to change color after exposure to atmospheric conditions for a number of days or a week. The color change sensor could be used with additional medical devices including catheters, vascular access devices, tubing connectors, blood bag, and the like.

As yet another example, the color change sensor could be used with a product such as makeup or medicine that has a shelf life of a certain period of time. For example, it has been found that cosmetic applicators can harbor bacteria that can infect the eye. The sensor of the present invention can be applied to the handle of a mascara applicator or eyeliner applicator, for example, so that, after the sensor is activated (e.g., the gas layer is removed), a warning message becomes visible at the recommended time of replacement, after a number of hours or a week. As such a user is warned that the cosmetic should be disposed of prior to its expiration to prevent eye infections such as conjunctivitis.

Similarly, a color change sensor could be placed on a medical bag for containing fluids such as blood. Once the bag is filled with the target fluid, the sensor is activated by the user allowing exposure of the color change indicator to atmospheric conditions. The indicator then provides, e.g., a shelf life indication, changing color after a predetermined amount of time after activation and indicating how long the fluid has been in the bag.

Figure 10:
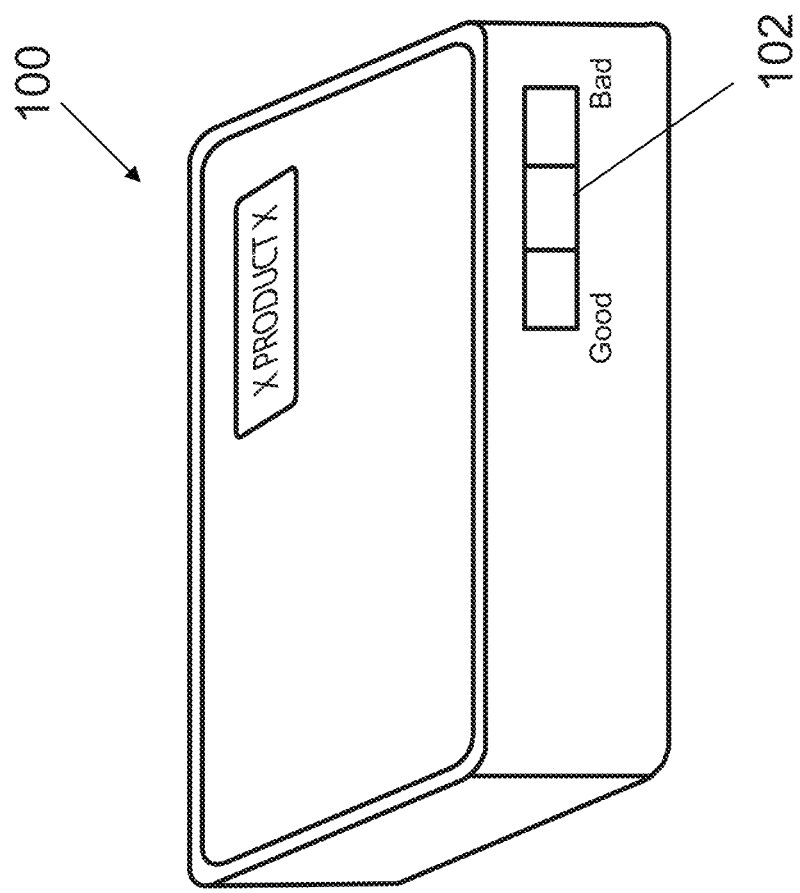
FIG. 10 is a perspective view of a packaging in accordance with one embodiment of the present application depicting an area of a sensor with sequential color change indicator inside the packaging and observable through the closed packaging.

In accordance with another embodiment of the present invention, a color change indication on a packaging provides accurate information or a warning to a user: that a product for human consumption within the packaging has reached its expiration time; that a product for human consumption has decreased in freshness, quality of taste or potency or that a product for human consumption within the packaging has been tampered with. The warning indication is provided by a sensor that changes color in a time controlled manner wherein the sensor is disposed on the packaging by being either printed on the packaging or incorporated within the material forming a portion of the packaging. The sensor may be safe for human consumption so that it can come into contact with the product for human consumption without any health concerns. The sensor can be disposed on the interior of the packaging while also being visible from the exterior of the packaging. Making the sensor visible from the exterior of the packaging allows the user to determine the environment on the interior of the packaging where the product for human consumption is contained without opening the packaging. For example, a packaging of the present application could contain a food product on the interior of the packaging. A portion of the food packaging could be a clear material with the color change sensor located on the interior of the clear portion. The sensor could then be viewed by the user from the exterior while measuring the environment on the interior with the food product. FIG. 10 is a perspective view of a packaging in accordance with one embodiment of the present invention depicting the color change indicator of the color changeable dye printed inside the packaging and observable through the closed packaging. In this embodiment, the internal sensor may be activated by crushing or otherwise destroying the gas layer on the sensor through the product packaging.

A sensor or multiple sensors may comprise a color change indicator or indicators with different compositions of dye, which can be disposed on the packaging in a sequential arrangement so the dye changes at different times to indicate a freshness or potency level as the freshness, quality of taste or potency changes. FIG. 10 illustrates an indicator scale showing the freshness, quality of taste or potency information of the product inside of the closed packaging. The indicator scale has different compositions of dye at the end of the scale that indicates "good" and the level that indicates "bad." The dyes will change at different times as the product's freshness, quality of taste or potency goes from good to bad. As an example of the sequential indicator, a food product could begin to decline in freshness or quality of taste after two weeks in an open package and continue the decline in an internal environment until its expiration date at one month. The dye at the "good" end of the scale could turn after two weeks, the dye at the middle end of the scale could turn at three weeks and the dye at the "bad" end of scale could turn at one month. This would indicate the level of freshness to the potential purchaser before they purchase and open the product. These specific times are only an example and could be changed to correspond to the internal product. Other words or symbols could be used in this indicator scheme and more levels of indication could be added.

In yet another embodiment of the invention, the sensor comprises sequential dye indicators printed on top of each other, and given that the indicator dye is relatively transparent until activated, the dyes may be printed such that a text message appears indicating the conditions within the packaging and that the previous message is blacked out by the newly activated indicator in the sequence.

As an example of this sequential indicator, a food product could begin to decline in freshness or quality of taste after two weeks in an open package and continue the decline in until its expiration date at one month. In this example, the term "good" could be written in a first dye that changes almost immediately after the food packaging is opened. A second dye which changes color after two weeks could be applied over the "good" indicator to black it out and the term "ok" could be written in the next area of the scale in that same dye. Finally, a third dye which changes color after four weeks could be applied over the "ok" indicator to black it out and the term "bad" could be written in the next area of the scale in the same dye. In this example, the potential purchaser would see the "good" indicator for the first two weeks when the product is freshest. That indicator would be blacked out after those two weeks and the potential purchaser would see the "ok" indicator during the two weeks after that when the product is starting to decline in freshness but has not yet expired. That indicator would be blacked out after four weeks and the potential purchaser would see the "bad" indicator. These specific times and oxygen levels are only an example and could be changed to correspond to the internal product. Other words or symbols could be used in this indicator scheme and more levels of indication could be added.

FIG. 10 is a perspective view of a packaging 100 in accordance with one embodiment of the present invention depicting the color change sensor 102 disposed inside the packaging and observable through the closed packaging.

In one embodiment more than one color change indicator can be used with a limited use, disposable or restricted use product. In this embodiment, each indicator can be used to indicate a different condition as, for example, described above. For example, the outside of a package may include a color change indicator exposed to atmospheric conditions that advises the user about the time that the product has been exposed to atmospheric conditions and whether the product has reached its expiration time while the product could also be used with a sensor comprising the gas layer and another color change indicator that is actuated by the user to advise the user how long a product has been used.

Figure 11:
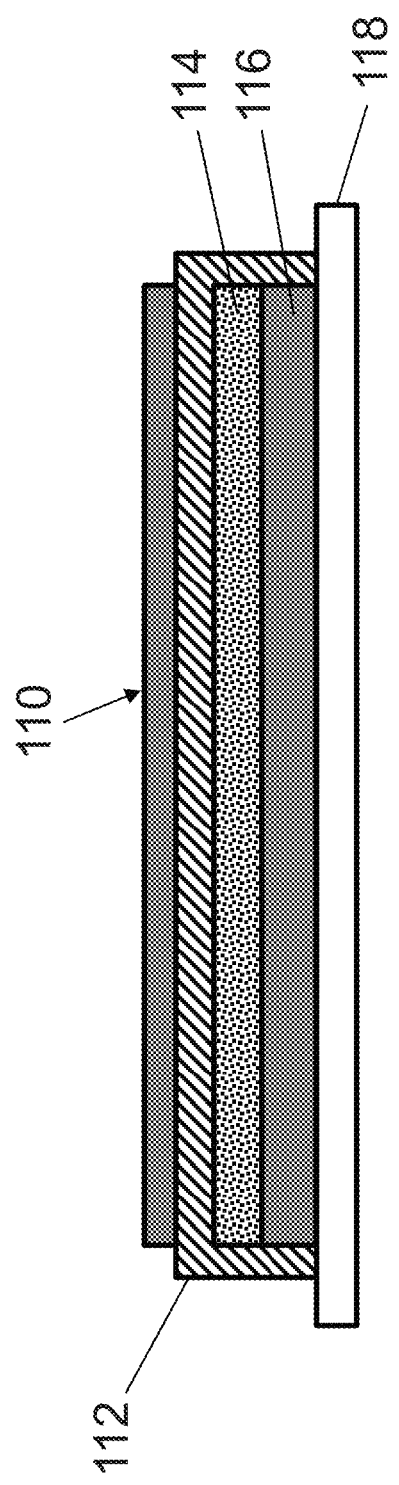
FIG. 11 is one embodiment of a color change sensor of the present invention with a second color change indicator disposed on the sensor.

FIG. 11 depicts a first color change indicator 110 disposed on an interface layer 112, which is disposed on a gas layer 114. The gas layer 114 is disposed on a second color change indicator 116. The sensor is disposed on a substrate 118, which is then applied to or used with a disposable, limited use, or restricted use product. In this embodiment, the first color change indicator 110 is exposed to atmospheric conditions and changes color if the product has reached its expiration period. Once the user has determined that the product is not expired by looking at the first color change indicator 110 and has decided to use the product associated with the sensor, the user removes or otherwise destroys the gas layer 114 underlying the first color change sensor 110 by, for example, peeling off or puncturing the first color change sensor 110, the interface layer 112, and the gas layer 114, exposing the second color change indicator 116. This actuates the second color change indicator 116, which allows the user to determine how long the product has been in use.

Figure 12:
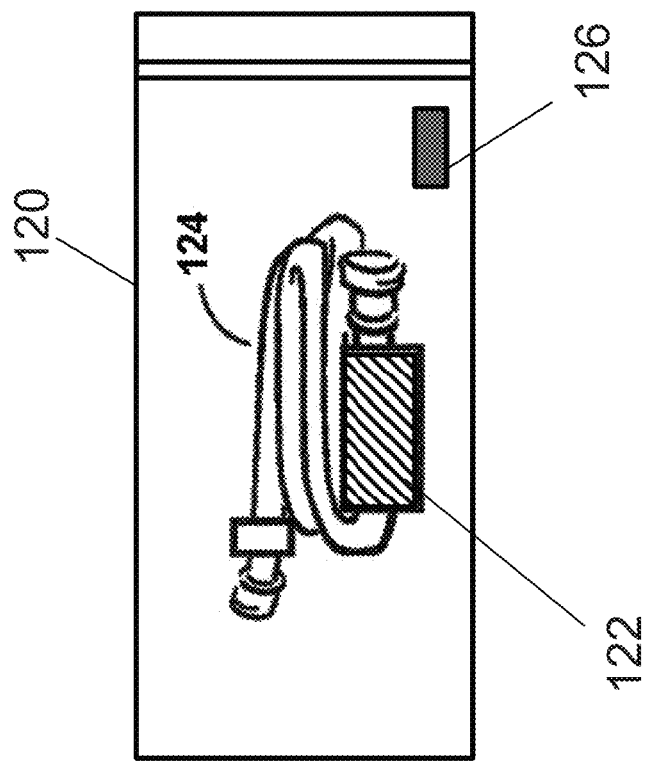
FIG. 12 is another embodiment of the present invention depicting a color change sensor disposed on a medical device and a second color change indicator disposed on a device package.
Figure 13A:
FIGS. 13A-L are color photographs of an exposure time indicator with a color changeable dye that changes color after exposure to an environment in a sequential manner.
Figure 13B:
Figure 13C:
Figure 13D:
Figure 13E:
Figure 13F:
Figure 13G:
Figure 13H:
Figure 13I:
Figure 13J:
Figure 13K:
Figure 13L:

FIG. 12 is another embodiment reflecting the use of two color change indicators. In this embodiment, a medical device such as catheter 124 is enclosed in product packaging 120. A sensor 122 comprising a gas layer and a first color change indicator is disposed on the medical device 124. A second color change indicator 126 is disposed inside the product packaging 120. The second color change indicator 126 indicates whether the package has been opened or otherwise exposed to atmospheric conditions. Once it is determined that the medical device is safe for use by observing the second color change indicator 126, the device is removed from the packaging 120. When the user is ready to use the device, perhaps at a time different than the time that the device was removed from the package, the user actuates the sensor 122 by, for example, peeling off or otherwise removing the gas layer and exposing the first color change indicator. The user then uses the device for the defined time indicated by the first color change indicator and the sensor 122 changes color when the medical device should no longer be used.

FIGS. 13A-L are photographs of an exposure time indicator utilizing stepped polymeric barriers with a color changeable carbon dioxide sensing dye that changes color in a sequential manner after being removed from a carbon dioxide rich environment and exposed to the intended use environment, e.g., an atmospheric environment. The stepped polymer sheets adhered over the paper indicator strip in the example are 0.002 inch thick cellulose. This device has nine regions with no sheets in the first region, one sheet in the second region, two sheets in the third region and so on. The region with no polymeric strips changes color in a matter of minutes. This can be seen in FIGS. 13A-13D. This rapid change indicates that the test strip is working and has been activated. Each 0.002 inch thick cellulose layer provides about a 2 hour barrier for the color changeable dye. The region with one strip changes color after approximately 2 hours, the region with two strips after approximately 4 hours and so on in a controlled sequential manner. This can be seen in FIGS. 13E-13K. The final region has 8 strips and changes after approximately 16 hours. This can be seen in FIG. 13L. This sequential change allows a user to ascertain the time that has elapsed since the disposable, limited or restricted use product has been opened and to anticipate the remaining time before replacement is required. As described above, this exposure time indicator can be the color change indicator used with the present invention.

While the application has been described with reference to certain embodiments, it will be understood by those skilled in the art that various changes may be made and equivalents may be substituted without departing from the scope of the application. In addition, many modifications may be made to adapt a particular situation or material to the teachings of the application without departing from its scope. Therefore, it is intended that the application not be limited to the particular embodiment disclosed, but that the application will include all embodiments falling within the scope of the appended claims.

The invention claimed is:

1. A color change sensor comprising:
a color change indicator for detecting an atmospheric gas, wherein the color change indicator is a dye that changes color when contacted by the atmospheric gas;
a gas-containing substrate disposed on the color change indicator, the gas-containing substrate comprising pores, matrices, or passages,
the gas-containing substrate containing non-atmospheric levels of a substrate gas dispersed in the pores, matrices, or passages to form a gas layer at the non-atmospheric levels of the substrate gas on at least a portion of the color change indicator prior to activation of the color change sensor, wherein the color change indicator does not change color when contacted by the non-atmospheric levels of the substrate gas, wherein the gas layer diffuses out of the gas-containing substrate after activation of the color change sensor to allow the atmospheric gas to reach the color change indicator, the gas layer inhibiting atmospheric levels of the atmospheric gas from contacting the color change indicator prior to activation of the color change sensor and delaying detection of the atmospheric gas by the color change indicator while the gas layer diffuses out of the gas-containing substrate; and
an interface layer inhibiting the escape of the gas layer from the gas-containing substrate prior to activation of the color change sensor, the interface layer disposed on at least a portion of the gas-containing substrate, wherein the color change sensor is activated by removing or disrupting at least a portion of the interface layer or by removing or disrupting at least a portion of the gas-containing substrate,
wherein the substrate gas is selected from the group consisting of ammonia, carbon dioxide, nitrogen, argon and/or oxygen, and the non-atmospheric levels of the substrate gas in the gas-containing substrate is different than the atmospheric levels of the atmospheric gas present in an environment surrounding the color change sensor.

2. The sensor of claim 1 wherein the color change indicator is a carbon dioxide-based indicator and the atmospheric gas is carbon dioxide.

3. The sensor of claim 1 wherein the color change indicator is an oxygen-based indicator and the substrate gas is carbon dioxide, argon, or nitrogen.

4. The sensor of claim 1 wherein the interface layer is disposed on the gas-containing substrate and the color change indicator.

5. The sensor of claim 4 wherein the sensor is disposed on a disposable, limited, or restricted use apparatus.

6. The sensor of claim 5 wherein the disposable, limited, or restricted use apparatus comprises a medical device.

7. The sensor of claim 5 wherein the sensor is disposed on or within product packaging.

8. The sensor of claim 4 wherein the color change indicator is disposed on a second substrate.

9. The sensor of claim 1 wherein the gas-containing substrate is a gas-containing matrix.

10. The sensor of claim 9 wherein the gas-containing matrix comprises polymethylmethacrylate, silicone, or urethane.

11. The sensor of claim 1 wherein an adhesive is disposed between the gas-containing substrate and the color change indicator.

12. The sensor of claim 1 wherein the gas-containing substrate is disposed directly on the indicator.

13. The sensor of claim 1 wherein the color change indicator is an exposure time indicator configured to change color in a sequential manner.

14. A kit comprising at least two of the sensors of claim 1.

15. The sensor of claim 1 wherein the sensor further comprises a second color change indicator.

16. The sensor of claim 15 wherein the sensor comprises an exposure time indicator configured to change color in a sequential manner and the second color change indicator is a carbon dioxide based indicator.

17. The sensor of claim 1 wherein the interface layer is disposed directly on the gas-containing substrate.

18. A kit comprising:
at least one gas-containing substrate that is porous or contains a matrix or passages and contains non-atmospheric levels of a substrate gas, and an interface layer disposed on the at least one gas-containing substrate inhibiting escape of the substrate gas from the gas-containing substrate; and
at least two color change indicators that are separate from one another in the kit for detecting at least one atmospheric gas, wherein the color change indicators are dyes that change color when contacted by the atmospheric gas, and wherein the color change indicators do not change color when contacted by the non-atmospheric levels of the substrate gas,
wherein the at least one gas-containing substrate has a surface that can be disposed on either of the at least two color change indicators to form a color change sensor, the gas-containing substrate forming a gas layer at non-atmospheric levels of the substrate gas on at least a portion of the respective color change indicator prior to activation of the color change sensor, the substrate gas diffusing out of the gas-containing substrate after activation of the color change sensor, the substrate gas inhibiting atmospheric levels of atmospheric gas from contacting the respective color change indicator prior to activation of the color change sensor and delaying detection of the atmospheric gas by the color change indicator while the gas layer diffuses out of the gas-containing substrate, wherein the color change sensor is activated by removing or disrupting at least a portion of the interface layer or by removing or disrupting at least a portion of the gas-containing substrate.

* * * * *